US008962918B2

(12) United States Patent
Datta et al.

(10) Patent No.: US 8,962,918 B2
(45) Date of Patent: Feb. 24, 2015

(54) POLYNUCLEOTIDE SEQUENCE OF FRUIT SOFTENING ASSOCIATED A-MANNOSIDASE AND ITS USES FOR ENHANCING FRUIT SHELF LIFE

(75) Inventors: Asis Datta, Gurgaon (IN); Subhra Chakraborty, New Delhi (IN); Niranjan Chakraborty, New Delhi (IN); Sumit Ghosh, New Delhi (IN); Vijaykumar Siddesh Meli, New Delhi (IN)

(73) Assignee: National Institute of Plant Genome Research, New Delhi (IN)

( * ) Notice: Subject to any disclaimer, the term of this patent is extended or adjusted under 35 U.S.C. 154(b) by 691 days.

(21) Appl. No.: 13/003,203

(22) PCT Filed: Jul. 9, 2009

(86) PCT No.: PCT/IN2009/000387
§ 371 (c)(1),
(2), (4) Date: Apr. 27, 2011

(87) PCT Pub. No.: WO2010/004582
PCT Pub. Date: Jan. 14, 2010

(65) Prior Publication Data
US 2011/0239325 A1    Sep. 29, 2011

(30) Foreign Application Priority Data

Jul. 9, 2008 (IN) .......................... 1647/DEL/2008

(51) Int. Cl.
C12N 15/82 (2006.01)
C12N 9/24 (2006.01)
A01H 5/00 (2006.01)
C12N 15/113 (2010.01)
C12N 15/52 (2006.01)
C12N 15/84 (2006.01)
C07H 21/02 (2006.01)

(52) U.S. Cl.
CPC .......... C12N 15/8249 (2013.01); C12N 9/2402 (2013.01); C12Y 302/01024 (2013.01)
USPC ........ 800/285; 800/295; 800/284; 800/317.1; 800/317.4; 435/468; 435/200; 435/320.1; 435/252.2; 435/252.33; 536/23.6; 536/24.5

(58) Field of Classification Search
None
See application file for complete search history.

(56) References Cited

FOREIGN PATENT DOCUMENTS

WO    WO 9924588    *   5/1999    ........... C12N 15/56

OTHER PUBLICATIONS

Strasser et al (The Plant Journal, vol. 47, Issue 5, 827, 2006; Strasser).*
Montoya et al (The Plant Cell, vol. 14, 3163-3176, Dec. 2002; Montoya).*
Gonzales et al (Mol. Biol. Evol. 17(2):292-300. 2000; Gonzales).*
Kusaba (Current Opinion in Biotechnology, 15, pp. 139-143, 2004).*
Hossain et al (J. Biochem, 148(5), pp. 603-616, 2010).*
*Arabidopsis thaliana* alpha-mannosidase (At5g13980) mRNA, complete cds, retrieved from EBI accession No. EMBL: AY099704 (May 7, 2002).
Brummell, Cell wall disassembly in ripening fruit, Functional Plant Biol., 33:103-19 2006).
Causier et al., MADS-box genes reach maturity, Science, 296:275-6 (Apr. 12, 2002).
Hendry et al., Induction of cytochrome P-450 in intact mung beans, New Phytol., 96:153-9 (1984).
Henrissat et al., A census of carbohydrate-active enzymes in the genome of *Arabidopsis thaliana*, Plant Molecular Biol., 47:55-72 (2001).
International Preliminary Report on Patentability for corresponding International Application No. PCT/IN2009/000387, dated Jan. 11, 2011.
Jagadeesh et al., Activities of glycosidases during fruit development and ripening of tomato (Lycopersicum esculantum L.): implication in fruit ripening, Plant Sci., 166:1451-9 (2004).
Jamet et al., Cell wall proteins: a new insight through proteomics, Trends in Plant Sci., 11(1):33-9 (Jan. 2006).
Orzaez et al., Agroinjection of tomato fruits. A tool for rapid functional analysis of transgenes directly in fruit, Plant Physiol., 140:3-11 (Jan. 2006).
Priem et al., Structure of Ten Free N-glycans in ripening tomato fruit, Plant Physiol., 102:445-58 (1993).
Sethu et al., α-D-mannosidase from *Capsicum annuum*, Phytochem., 44(3):383-7 (1997).
Suvarnalatha et al., α-D-mannosidase from Lycopersicon esculentum II, Phytochem., 50:1111-5 (1999).
Watkins et al., Activities of polygalacturonase, α-D-mannosidase, and α-D- and -βD-galactosidases in ripening tomato, HortScience, 23(10):192-4 (1988).
Wesley et al., Construct design for efficient, effective and high-throughput gene silencing in plants, The Plant Journal, 27(6):581-90 (2001).

* cited by examiner

*Primary Examiner* — David T Fox
*Assistant Examiner* — Stephen Uyeno
(74) *Attorney, Agent, or Firm* — Marshall, Gerstein & Borun LLP

(57) ABSTRACT

The present invention provides isolated polynucleotide sequences encoding α-mannosidase. The present invention further provides DNA constructs comprising the polynucleotide sequence coding for α-mannosidase in sense or anti-sense orientation, RNAi constructs, recombinant vectors comprising the constructs, and host cells comprising the recombinant vector. The present invention further provides transgenic plants, plant cells, transgenic progeny and seeds expressing the polynucleotide with reduced α-mannosidase protein accumulation, having enhanced fruit shelf life.

19 Claims, 9 Drawing Sheets

Figure 1:
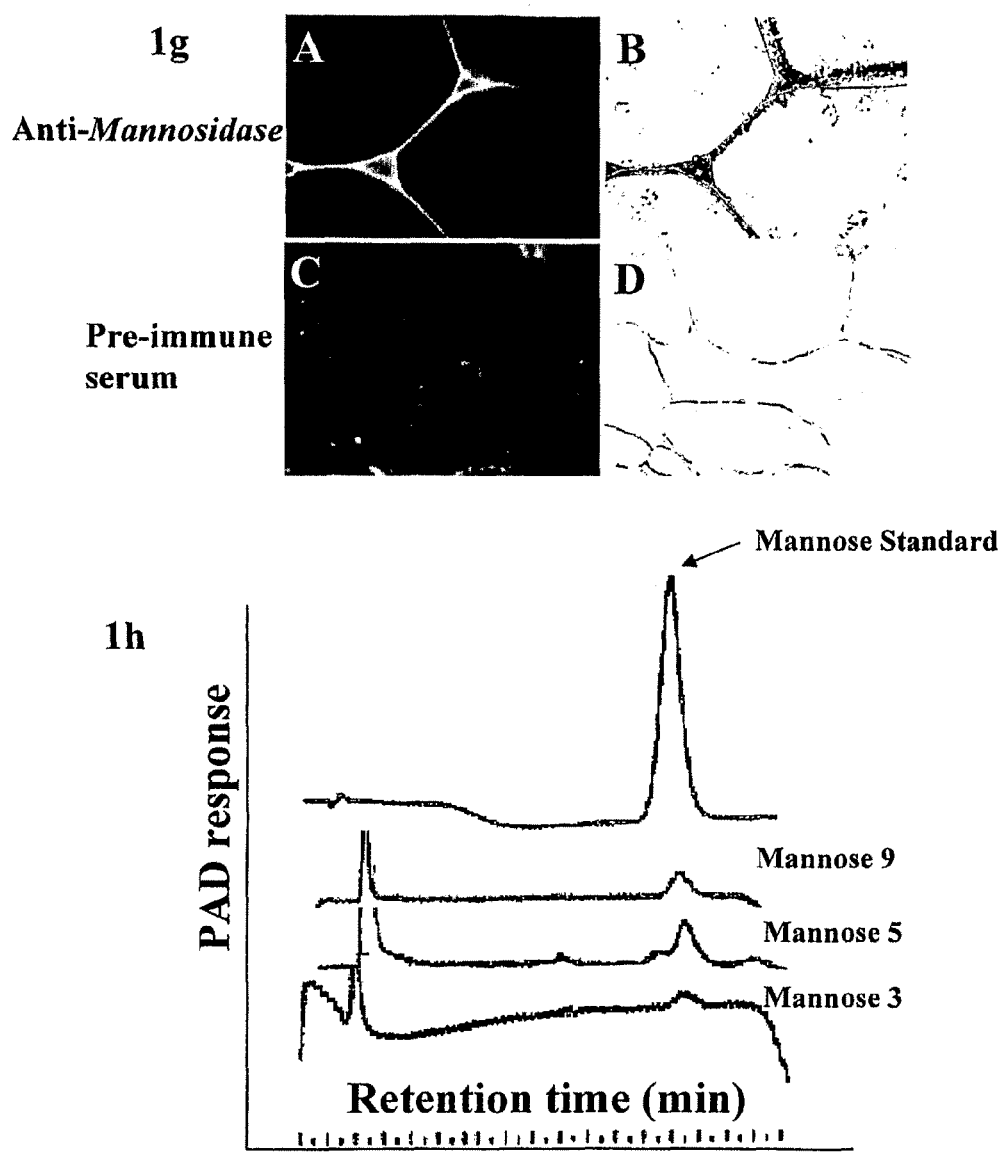

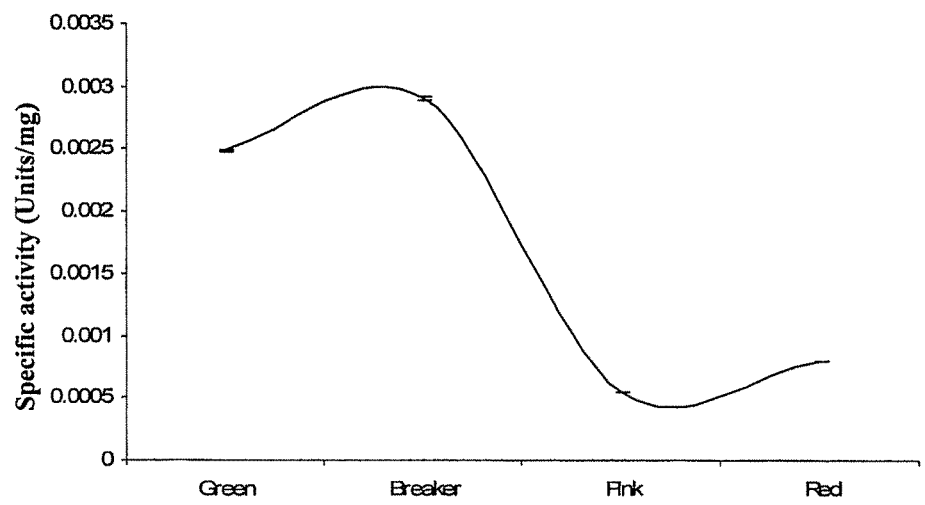
1a
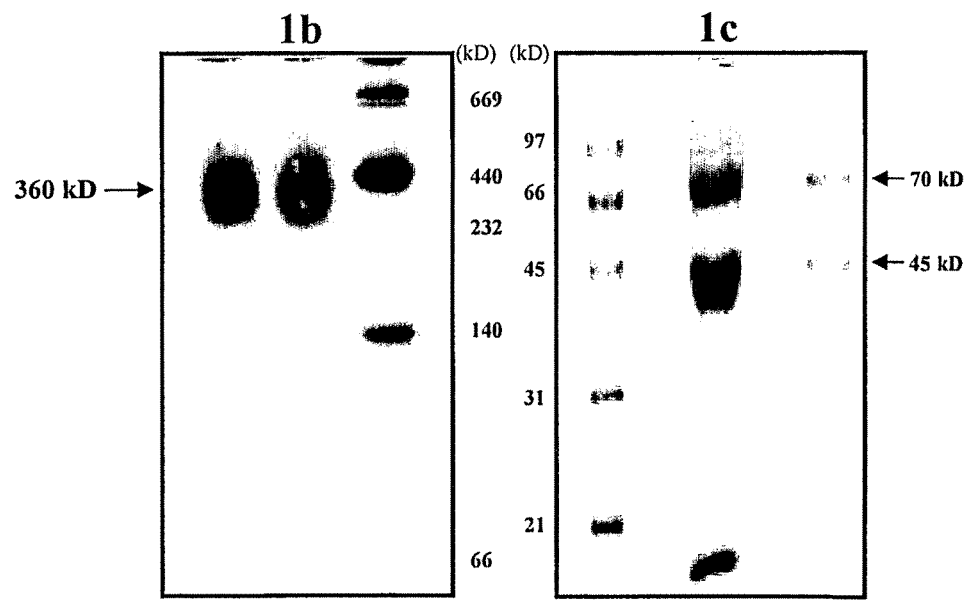

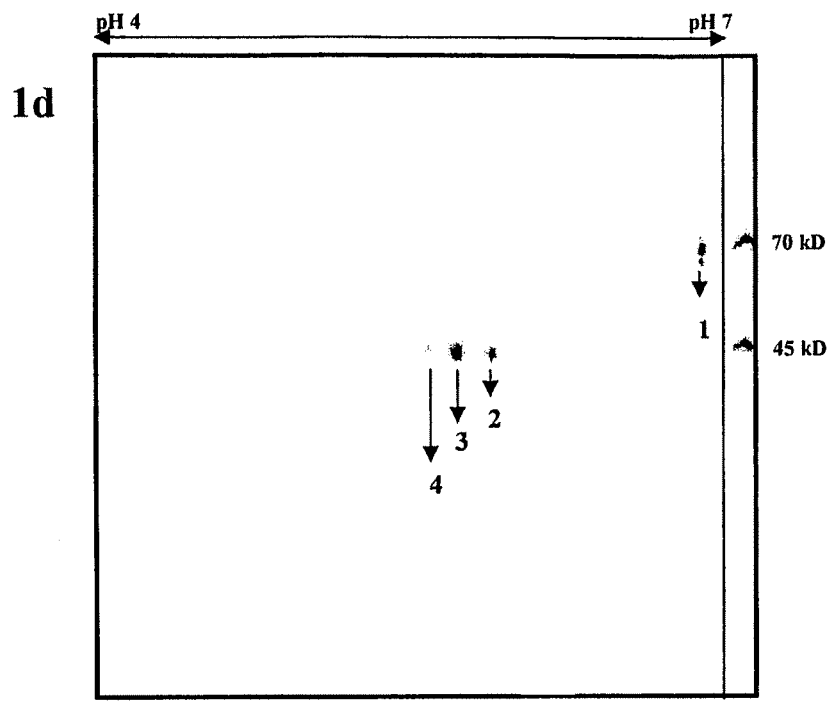
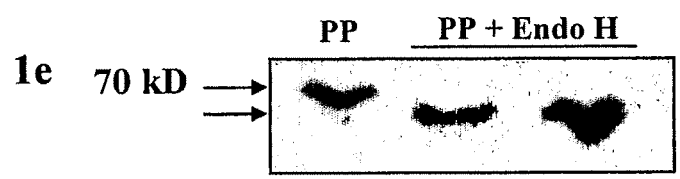
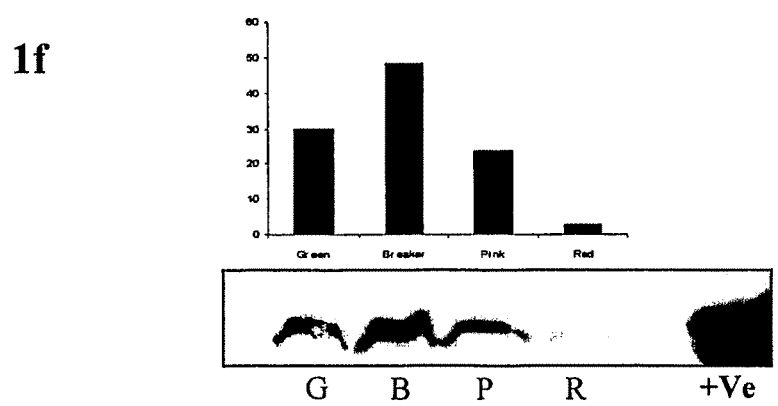

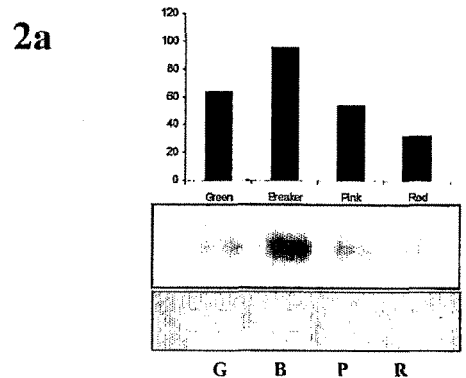
2a
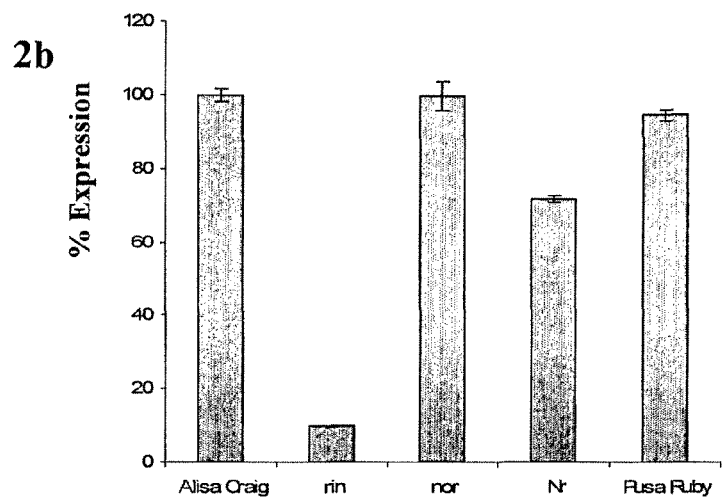
2b
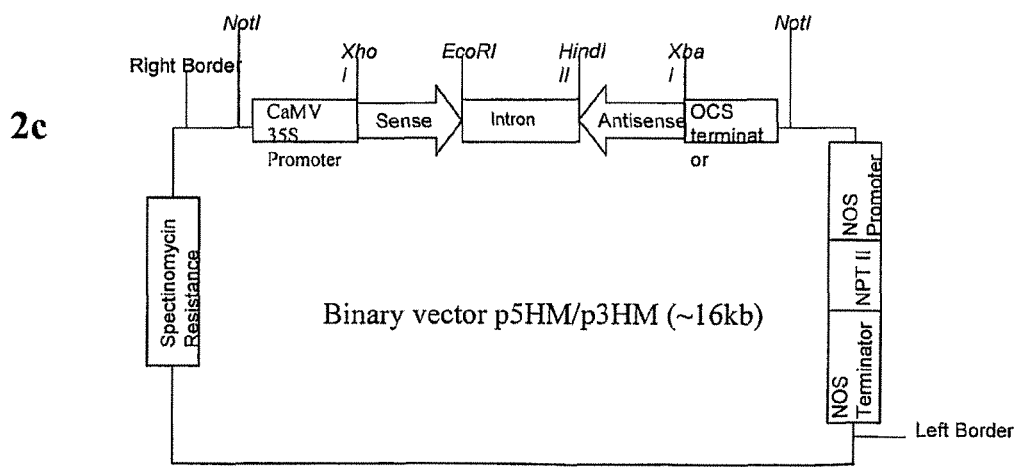
2c

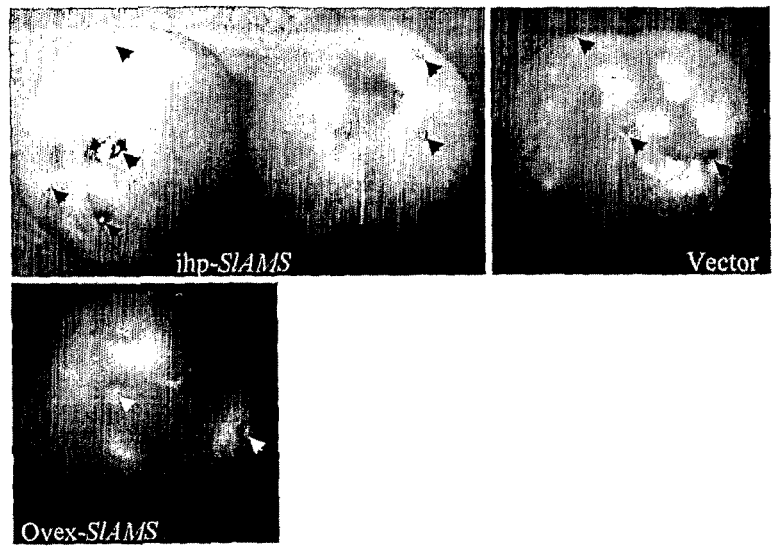
3a
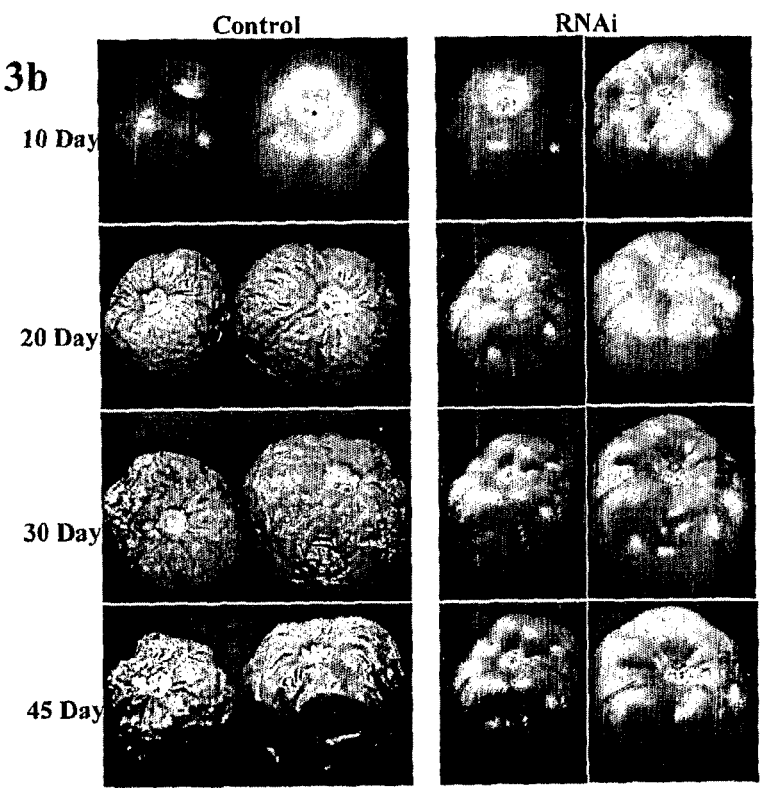
3b

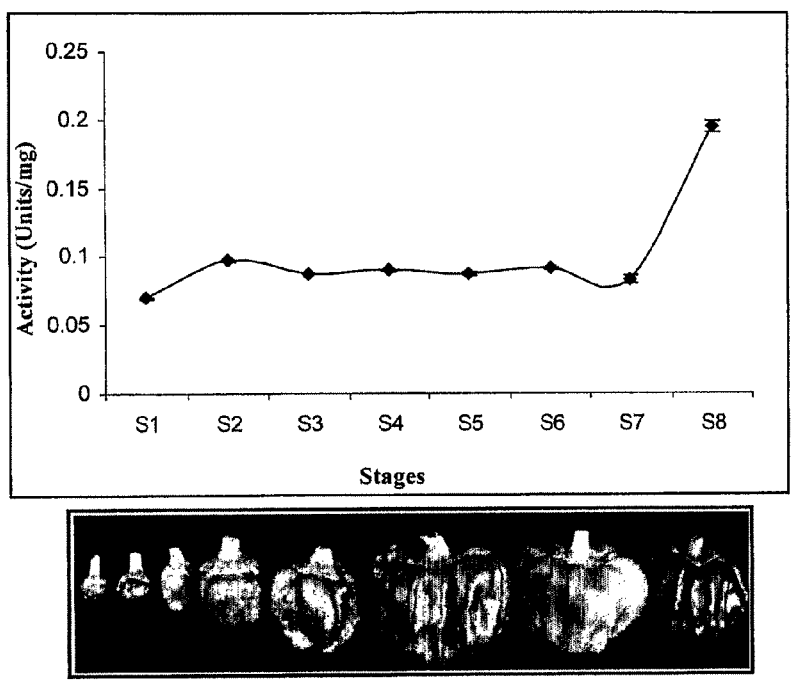
4a

SEQUENCE LISTING

<160> NUMBER OF SEQ ID NOS: 18

<210> SEQ ID NO 1
<211> LENGTH: 3411
<212> TYPE: DNA
<213> ORGANISM: Solanum lycopersicum
<220> FEATURE:
<221> NAME/KEY: misc_feature
<223> OTHER INFORMATION: c-DNA sequence of Solanum lycopercicum
      alpha-mannosidase including 5' and 3' UTR region

<400> SEQUENCE: 1

```
gagagatttg gggtttatgg tttagtacat tctctttcag tgaacactct cagcaattgt    60
ggaaatgaaa aatatgggga agtttgaaat ttggttcttg attttgatgg tttgtgggtt   120
gtgggtagtg gaagctaagt atatggttta caatacatca cagggaattg tttcagggaa   180
gcttaacgtt catttggttc ctcacactca cgatgatgtt ggctggttga aaacggtcga   240
tcagtactat gttggttcca acaattccat tcaggtggct tgtgttcaaa atgtcttgga   300
ttcattgatt ccagcattat tggctgataa aaacagaaag ttcattttatg ttgaacaggc   360 tttttttccag cgttggtgga ggaatcagag cccgggaatg cagagcacag tcaaacagct   420
cgtcaactcg ggtcaacttg agtccataaa tggaggttgg tgcatgcatg atgaggcagc   480
aacacattat attgacatga tagatcagac aactctaggg cataaataca tcaaacaaca   540
gttcaatgtt actcctagaa ttggctggca aatcgaccct tttgggacat tctgctgttc   600
aggcatacct tctgggagca agggttggat tcgactctct tttctttggg acgcattgac   660
taccaaggac agagaaaaga ggaaaattga gaagagccctt gaggtcattt ggaggggttc   720
taagagtctc agttcatcca cgcaaatatt ttcaggtgca ttccctcaga attatgaacc   780
tcccagcaaa ttttactttg aagtgaatga tgataattct cttcctgttc aggatgatgt   840
caacctgttt gactacaatg tccaagagcg ggtcaatgac tttgttgctg ctgctttgtc   900
ccaagccaat atcactcgca caaatcatat aatgtggacc atgggaaccg acttcaagta   960
ccaatatgct catacatggt ttcggaatat ggacaagctc attcactacg taaaccaaga  1020
tggtcgtgtc aatgctttat attcaagccc ttcaatttat actgatgcaa agtatgcttt  1080
ggacgagtca tggcctctca agacggatga ctatttcccg tacgcagacc gtattaatgc  1140
ttattggact ggatacttta caagtaggcc tgctctcaaa ctctatgtta gaatgatgag  1200
tggctattat ttggcagcaa ggcaattaga attctttaaa ggaagaattg agacaggacc  1260
aacaaccgaa atattggctg atgccctagc catcgctcaa catcatgatg ctgtcagtgg  1320
cactccaaag caacatgttg ctgatgatta tgccaaacga ctgttcatag ttacaagca   1380 ggctgaggat ttagtgtcta attcacttgc ttgtatggtg aatcagcttt cagcatctgg  1440
atgcaagaat cctcagataa atttcaagca gtgcccgttg ttgaatataa gttattgtcc  1500
cccaacagaa gctgatcttg ctccaggcaa aaaattagtg gttgtcgtgt acaatgctct  1560
tgggtggaaa agaacagatg ttgtcagaat ccctgtcgtc aataagaatg tcatcgttga  1620
```

-continued

```
ggattccact ggaaaagaaa ttgaatcaca gcttcttcca atagttaaag aatcaatagt  1680
aataaggaac tactatgctg cagcatactt tggtgaatcc cctacatcaa gccccaaata  1740
ttggcttgtg tttacagcca ctgttccacc tttgggcttt agctcctatg ttataacaag  1800
tggtaaacaa gcagttgctg cttcaatacc acagacgttc tacaaaactg atggaagtca  1860
aagtgatgca gtagaagtgg ggccggggaa cttgaaactg ttatattctg caaatggggc  1920
aaagtttact caatatttta ataagagaaa ccaggttaga agctctttgg agcaatcatt  1980
cagttattat tctgcagacg atggaagcaa ggatgattat aaagacattc aggcatctgg  2040
agcatatgtg tttcgcccaa acggctcatt ccccatccac cctgagggaa aggtcccagc  2100
taccattcta cgaggtccgc tgctagatga agttcatcaa aatatcaatt catggatata  2160
tcagatcact agagtgtaca aggaaaagga gcacgttgaa gttgagttca ctgttggccc  2220
cataccattt gacaatggaa ttgggaaaga gctggtgact cagattcaaa ctgacatcaa  2280
aagcaacaaa acattctaca gagactctaa tggacgtgat ttccttaaaa gagttcggga  2340
ttatagagct gactgggatc ttcaagtgaa ccaacctgct gctggaaatt attatcctat  2400
caatcttgga ctttttccta aggacaacaa caacgagttc tcagttttgg ttgatagatc  2460
tgtaggtgga tccagccttg ttgatggcca attggagcta atgcttcacc ggaggttact  2520
caatgatgat ggaagaggtg ttgctgaagc actgaatgaa accgtctgtg ctcttggaaa  2580
atgcatgggc ttgactgtcc aaggcaagta ctatatccgg attgattctc ttggagaggg  2640
agcgaaatgg cggcggtcat ttggacagga gatatattct ccattgcttc tagcttttac  2700
tgagcaggat ggagataaat ttacaaaatt tccagttcca acctttacag ggatggaccc  2760
atcttacagt ctgcctgata atgttgcaat aattacgctt caggagcttg aagatcacac  2820
cgtcctcctg agattggctc atttatacga ggttgatgag gataaggatc tatccaccaa  2880
ggcaagtgta gaattgaaaa gattgttccc aaagaggaag ataaacaaga ttagagagat  2940
gagtttatct gccaaccaag aaagagtaga atggagaag aagagattaa agtggaaagc  3000
agaggctcct agtgatttgc gagacgtggc aagaggggga cctgttgatc ctacaaagct  3060
gatggtagag ctcgccccaa tggaaattcg cacctttgtt attgatctca gccagagcgt  3120
gccagaaggt tggaagtcac atatgtctct atgatagcag tctcctgcag cagtccaatc  3180
caatccgaat cgtcaagacg tcaaaagggt atatgagcag cttgaaacct tcttgggacc  3240
tatttgcctg tgttgatatc accttgagga ggcagcattg agtctcttgt tagaagatgt  3300
gttatccttt ttgtaatgga atgaaaacct ctttgacaga acaataaact tataataata  3360
ataatgatgt tgaagagaga acttccatgt cttagcaaaa aaaaaaaaa a           3411
```

<210> SEQ ID NO 2
<211> LENGTH: 1029
<212> TYPE: PRT
<213> ORGANISM: Solanum lycopersicum
<220> FEATURE:
<221> NAME/KEY: MISC_FEATURE
<223> OTHER INFORMATION: Protein sequence of alpha mannosidase

<400> SEQUENCE: 2

```
Met Lys Asn Met Gly Lys Phe Glu Ile Trp Phe Leu Ile Leu Met Val
1               5                   10                  15

Cys Gly Leu Trp Val Val Glu Ala Lys Tyr Met Val Tyr Asn Thr Ser
            20                  25                  30

Gln Gly Ile Val Ser Gly Lys Leu Asn Val His Leu Val Pro His Thr
```

```
                35                  40                  45
His Asp Asp Val Gly Trp Leu Lys Thr Val Asp Gln Tyr Tyr Val Gly
 50                  55                  60

Ser Asn Asn Ser Ile Gln Val Ala Cys Val Gln Asn Val Leu Asp Ser
 65                  70                  75                  80

Leu Ile Pro Ala Leu Leu Ala Asp Lys Asn Arg Lys Phe Ile Tyr Val
                 85                  90                  95

Glu Gln Ala Phe Phe Gln Arg Trp Trp Arg Asn Gln Ser Pro Gly Met
                100                 105                 110

Gln Ser Thr Val Lys Gln Leu Val Asn Ser Gly Gln Leu Glu Ser Ile
                115                 120                 125

Asn Gly Gly Trp Cys Met His Asp Glu Ala Ala Thr His Tyr Ile Asp
                130                 135                 140

Met Ile Asp Gln Thr Thr Leu Gly His Lys Tyr Ile Lys Gln Gln Phe
145                 150                 155                 160

Asn Val Thr Pro Arg Ile Gly Trp Gln Ile Asp Pro Phe Gly Thr Phe
                165                 170                 175

Cys Cys Ser Gly Ile Pro Ser Gly Ser Lys Gly Trp Ile Arg Leu Ser
                180                 185                 190

Phe Leu Trp Asp Ala Leu Thr Thr Lys Asp Arg Glu Lys Arg Lys Ile
                195                 200                 205

Glu Lys Ser Leu Glu Val Ile Trp Arg Gly Ser Lys Ser Leu Ser Ser
210                 215                 220

Ser Thr Gln Ile Phe Ser Gly Ala Phe Pro Gln Asn Tyr Glu Pro Pro
225                 230                 235                 240

Ser Lys Phe Tyr Phe Glu Val Asn Asp Asp Asn Ser Leu Pro Val Gln
                245                 250                 255

Asp Asp Val Asn Leu Phe Asp Tyr Asn Val Gln Glu Arg Val Asn Asp
                260                 265                 270

Phe Val Ala Ala Leu Ser Gln Ala Asn Ile Thr Arg Thr Asn His
                275                 280                 285

Ile Met Trp Thr Met Gly Thr Asp Phe Lys Tyr Gln Tyr Ala His Thr
290                 295                 300

Trp Phe Arg Asn Met Asp Lys Leu Ile His Tyr Val Asn Gln Asp Gly
305                 310                 315                 320

Arg Val Asn Ala Leu Tyr Ser Ser Pro Ser Ile Tyr Thr Asp Ala Lys
                325                 330                 335

Tyr Ala Leu Asp Glu Ser Trp Pro Leu Lys Thr Asp Asp Tyr Phe Pro
                340                 345                 350

Tyr Ala Asp Arg Ile Asn Ala Tyr Trp Thr Gly Tyr Phe Thr Ser Arg
                355                 360                 365

Pro Ala Leu Lys Leu Tyr Val Arg Met Met Ser Gly Tyr Tyr Leu Ala
                370                 375                 380

Ala Arg Gln Leu Glu Phe Phe Lys Gly Arg Ile Glu Thr Gly Pro Thr
385                 390                 395                 400

Thr Glu Ile Leu Ala Asp Ala Leu Ala Ile Ala Gln His His Asp Ala
                405                 410                 415

Val Ser Gly Thr Pro Lys Gln His Val Ala Asp Tyr Ala Lys Arg
                420                 425                 430

Leu Phe Ile Gly Tyr Lys Gln Ala Glu Asp Leu Val Ser Asn Ser Leu
                435                 440                 445

Ala Cys Met Val Glu Ser Ala Ser Ala Ser Gly Cys Lys Asn Pro Gln
450                 455                 460
```

```
Ile Asn Phe Lys Gln Cys Pro Leu Leu Asn Ile Ser Tyr Cys Pro Pro
465                 470                 475                 480

Thr Glu Ala Asp Leu Ala Pro Gly Lys Lys Leu Val Val Val Val Tyr
                485                 490                 495

Asn Ala Leu Gly Trp Lys Arg Thr Asp Val Val Arg Ile Pro Val Val
                500                 505                 510

Asn Lys Asn Val Ile Val Glu Asp Ser Thr Gly Lys Glu Ile Glu Ser
                515                 520                 525

Gln Leu Leu Pro Ile Val Lys Glu Ser Ile Val Ile Arg Asn Tyr Tyr
                530                 535                 540

Ala Ala Ala Tyr Phe Gly Glu Ser Pro Thr Ser Ser Pro Lys Tyr Trp
545                 550                 555                 560

Leu Val Phe Thr Ala Thr Val Pro Pro Leu Gly Phe Ser Ser Tyr Val
                565                 570                 575

Ile Thr Ser Gly Lys Gln Ala Val Ala Ala Ser Ile Pro Gln Thr Phe
                580                 585                 590

Tyr Lys Thr Asp Gly Ser Gln Ser Asp Ala Val Glu Val Gly Pro Gly
                595                 600                 605

Asn Leu Lys Leu Leu Tyr Ser Ala Asn Gly Ala Lys Phe Thr Gln Tyr
                610                 615                 620

Phe Asn Lys Arg Asn Gln Val Arg Ser Ser Leu Glu Gln Ser Phe Ser
625                 630                 635                 640

Tyr Tyr Ser Ala Asp Asp Gly Ser Lys Asp Asp Tyr Lys Asp Ile Gln
                645                 650                 655

Ala Ser Gly Ala Tyr Val Phe Arg Pro Asn Gly Ser Phe Pro Ile His
                660                 665                 670

Pro Glu Gly Lys Val Pro Ala Thr Ile Leu Arg Gly Pro Leu Leu Asp
                675                 680                 685

Glu Val His Gln Asn Ile Asn Ser Trp Ile Tyr Gln Ile Thr Arg Val
                690                 695                 700

Tyr Lys Glu Lys Glu His Val Glu Val Glu Phe Thr Val Gly Pro Ile
705                 710                 715                 720

Pro Ile Asp Asn Gly Ile Gly Lys Glu Leu Val Thr Gln Ile Gln Thr
                725                 730                 735

Asp Ile Lys Ser Asn Lys Thr Phe Tyr Thr Asp Ser Asn Gly Arg Asp
                740                 745                 750

Phe Leu Lys Arg Val Arg Asp Tyr Arg Ala Asp Trp Asp Leu Gln Val
                755                 760                 765

Asn Gln Pro Ala Ala Gly Asn Tyr Tyr Pro Ile Asn Leu Gly Leu Phe
                770                 775                 780

Leu Lys Asp Asn Asn Glu Phe Ser Val Leu Val Asp Arg Ser Val
785                 790                 795                 800

Gly Gly Ser Ser Leu Val Asp Gly Gln Leu Glu Leu Met Leu His Arg
                805                 810                 815

Arg Leu Leu Asn Asp Asp Gly Arg Gly Val Ala Glu Ala Leu Asn Glu
                820                 825                 830

Thr Val Cys Ala Leu Gly Lys Cys Met Gly Leu Thr Val Gln Gly Lys
                835                 840                 845

Tyr Tyr Ile Arg Ile Asp Ser Leu Gly Glu Gly Ala Lys Trp Arg Arg
                850                 855                 860

Ser Phe Gly Gln Glu Ile Tyr Ser Pro Leu Leu Leu Ala Phe Thr Glu
865                 870                 875                 880
```

```
Gln Asp Gly Asp Lys Phe Thr Lys Phe Pro Val Pro Thr Phe Thr Gly
                885                 890                 895

Met Asp Pro Ser Tyr Ser Leu Pro Asp Asn Val Ala Ile Ile Thr Leu
        900                 905                 910

Gln Glu Leu Glu Asp His Thr Val Leu Leu Arg Leu Ala His Leu Tyr
    915                 920                 925

Glu Val Asp Glu Asp Lys Asp Leu Ser Thr Lys Ala Ser Val Glu Leu
930                 935                 940

Lys Arg Leu Phe Pro Lys Arg Lys Ile Asn Lys Ile Arg Glu Met Ser
945                 950                 955                 960

Leu Ser Ala Asn Gln Glu Arg Val Glu Met Glu Lys Lys Arg Leu Lys
                965                 970                 975

Trp Lys Ala Glu Ala Pro Ser Asp Leu Arg Asp Val Ala Arg Gly Gly
            980                 985                 990

Pro Val Asp Pro Thr Lys Leu Met  Val Glu Leu Ala Pro  Met Glu Ile
        995                 1000                1005

Arg Thr  Phe Val Ile Asp Leu  Ser Gln Ser Val Pro  Glu Gly Trp
    1010                1015                1020

Lys Ser  His Met Ser Leu
    1025
```

<210> SEQ ID NO 3
<211> LENGTH: 3477
<212> TYPE: DNA
<213> ORGANISM: Capsicum annuum
<220> FEATURE:
<221> NAME/KEY: misc_feature
<223> OTHER INFORMATION: cDNA seqence of Capsicum annuum
      alpha-mannosidase including 5' and 3' UTR region

<400> SEQUENCE: 3

```
gaattttatt tggtatttat ttccaattaa ttaattaatt aatgtagtag taggtccttt      60
gtctttgatt ccccttcatg ttttgtctac aaatttcagc agcctattta taaagacatt     120
gagtgcacac tcatagcaaa tttgtgaaat gaaagatatg gctaagtgtg aaatttggtt     180
cttgattttg atgctttgtg ggttggtggt ggaagcaaag tatatggttt acaatacatc     240
acaaagcatt gttaagggaa gcttaatgt tcatttggtt cctcacagtc atgatgatgt     300
tggctggttg aaaactatcg atcagtacta tgttggatcc aataattcca ttcagggagc     360
ttgtgttgaa aatgtcttgg attcaatggt tccagcatta ttggctgata aaaaccggaa     420
gttcatttat gttgaacagg cttttttcca gcgttggtgg aggaatcaga gccccgaaat     480
tcagagcaca gttaggcagc ttatcaactc gggtcaactt gagttcataa acggaggttg     540
gtgcatgcat gacgaggcag cgacacatta tattgacatg atagatcaga caactctagg     600
gcacagatac atcaaacaac agttcaatat tgctccaaga attggctggc aaattgaccc     660
ttttggacat tctgctgttc aggcatacct tctgggagca gaggttggat tcgactctct     720
tttctttgga cgcattgact accaagacag agaaaagagg aaaattgaga gagccttga     780
ggtcatttgg aggggttcta agagtctcag ttcatccacg caaatatttt caggtgcatt     840
ccctcagaat tatgaacctc ccagcaaatt ttactttgaa gtgatgatg ataattctct     900
tcctgttcag gatgatgtca acctgtttga ctataatgtc caagagcggg tcaatgactt     960
tgttgctgct gctttgtccc aagccaatat cactcgcaca aatcatataa tgtggaccat    1020
gggaaccgac ttcaagtacc aatatgctca tacatggttt cggaatatgg acaagttcat    1080
tcactacgta aaccaagatg gtcgtgtcaa tgctttatat tcaagccctt caatttatac    1140
```

```
tgatgcaaag tatgctttgg acgagtcatg gcctctcaag acgggtgact atttcccgta    1200
cgcagaccgt attaatgctt attggactgg atactttaca agtaggcctg ctctcaaact    1260
ctatgttaga atgatgagtg gctattattt ggcagcaagg caattagaat tctttaaagg    1320
aagaagtgag acaggaggac caacaaccga agtgttggct gatgcgcttg ccattgccca    1380
gcatcatgat gctgtcagtg gcacttcaaa gcaacatgtt gctgatgatt atgccaaacg    1440
actgttcata ggttacaagc aggctgagga tatagtgtca aattcactcg cttgtatggt    1500
ggaaccagct tcagcatctg gatgcaagaa tcctcggatt aatttcaagc agtgcccatt    1560
gttgaatata agttattgtc ccccaacaga agctgatctt gctcctggca aaaaattagt    1620
ggttgtcgtg tacaatgctc ttgggtggaa aagaacagat gttgtcagaa tccctgttgt    1680
caataagaat gtcatcattc aggattccac tggaaaagaa attgaatcac agcttcttcc    1740
aatagttaaa gcttcaatag caataaggaa ctactatgct accgcatatg ttggtgaatc    1800
acctacatca agccccagat attggctcgt gtttacagct actgttccac cattgggctt    1860
taactcctac attatatcaa gtggtaaaca agcagttgct gcttcaatac cacagtcttt    1920
ctacaaaact gatggaagtc aaagtgatgt tatagaagtg gggcccggga acttgaaact    1980
gttatattct gcaaatgggg gaaagttcac tcaatatttt aataagagaa accaggttag    2040
aagctctctg gagcaatcat tcagttatta ttctgcagat gatggaagca aggatgctta    2100
taaagacatt caggcctctg ggcatatgt gtttcgtcca aatggctcat tccccatcca    2160
ccccgaggga aaggttccag ctaccattct gcgaggtccg ctgctagatg aagttcatga    2220
aaatattaat tcatggatat atcagatcac tagagtgtac aaggagaagg agcacgttga    2280
agttgagttc actgttggcc ccataccta  tgacaatgga attgggaaag agctggtgac    2340
tcagattcaa actgacatca aaagcaacaa aacattctac accgactcta atggacgtga    2400
tttcctcaaa aggattcggg attacagagc tgattgggat cttcaagtga accaacctgc    2460
tgctggaaat tattatccta ttaatcttgg aattttcctg aaagacgaca gcaacgagtt    2520
ctcagttttg gttgatagat ctgtaggtgg atccagcctt gttgatggcc aattggagct    2580
aatgcttcac cggaggttac tccatgatga tggaagaggg gttgctgaag cactgaatga    2640
aacagtctgt gctcttggaa aatgcatggg cttgactgtc caaggcaagt actatatccg    2700
gattgattct ctgggagagg gagcaaagtg gcggaggtca tttggacagg agatatattc    2760
tccgttgctt ctagctttta ctgagcagga tggagataaa tttacaaaat ttccagttcc    2820
aacatttaca tggatagatc catcttacag tctgcctgat aatgttgcaa taatcaccct    2880
tcaggagctt gaagatcaca ctgtcctcct cagattggct catttatacg aggttgatga    2940
ggataaggat ctgtccacca aggcaattgt agaattgaag agattgttcc caaagagaaa    3000
gataaacaag attaaagaga tgagtttatc tgccaaccaa gaaagagaag aaatggaaaa    3060
gaagagattg aagtggaaag cagaggctcc tagtgattcg caagacgtgc caagagggga    3120
acctgttgat cctacaaagt tggtggtgga gcttgcccca atggaaatcc gcactttcgt    3180
tatcaacctc ggccagagct cgccagctcc aggaggttgg aagtcacaca tgtctctatg    3240
atagcggtgc ccctgaaaca gtccaatccg attcggctag acagcaaaag ggtatgggca    3300
gcttgaaacc tacttgggac ctatttgcct atgttgatcc ttgaggatgc aacattgagt    3360
ctcttgttgg aagatgtgtt atccttttg  tataaggaat gaaaacctct ttggcagaac    3420
aataacttac tctataataa taaataataa tgttgaagag aaaaaaaaaa aaaaaaa      3477
```

<210> SEQ ID NO 4
<211> LENGTH: 1030
<212> TYPE: PRT
<213> ORGANISM: Capsicum annuum
<220> FEATURE:
<221> NAME/KEY: MISC_FEATURE
<223> OTHER INFORMATION: Protein sequence of alpha-mannosidase

<400> SEQUENCE: 4

```
Met Lys Asp Met Ala Lys Cys Glu Ile Trp Phe Leu Ile Leu Met Leu
1               5                   10                  15

Cys Gly Leu Val Val Glu Ala Lys Tyr Met Val Tyr Asn Thr Ser Gln
            20                  25                  30

Ser Ile Val Lys Gly Lys Leu Asn Val His Leu Val Pro His Ser His
        35                  40                  45

Asp Asp Val Gly Trp Leu Lys Thr Ile Asp Gln Tyr Tyr Val Gly Ser
    50                  55                  60

Asn Asn Ser Ile Gln Gly Ala Cys Val Glu Asn Val Leu Asp Ser Met
65                  70                  75                  80

Val Pro Ala Leu Leu Ala Asp Lys Asn Arg Lys Phe Ile Tyr Val Glu
                85                  90                  95

Gln Ala Phe Phe Gln Arg Trp Trp Arg Asn Gln Ser Pro Glu Ile Gln
            100                 105                 110

Ser Thr Val Arg Gln Leu Ile Asn Ser Gly Leu Glu Phe Ile Asn
        115                 120                 125

Gly Gly Trp Cys Met His Asp Glu Ala Ala Thr His Tyr Ile Asp Met
    130                 135                 140

Ile Asp Gln Thr Thr Leu Gly His Arg Tyr Ile Lys Gln Gln Phe Asn
145                 150                 155                 160

Ile Ala Pro Arg Ile Gly Trp Gln Ile Asp Pro Phe Gly His Ser Ala
                165                 170                 175

Val Gln Ala Tyr Leu Leu Gly Ala Glu Val Gly Phe Asp Ser Leu Phe
            180                 185                 190

Phe Gly Arg Ile Asp Tyr Gln Asp Arg Glu Lys Arg Lys Ile Glu Lys
        195                 200                 205

Ser Leu Glu Val Ile Trp Arg Gly Ser Lys Ser Leu Ser Ser Ser Thr
    210                 215                 220

Gln Ile Phe Ser Gly Ala Phe Pro Gln Asn Tyr Glu Pro Pro Ser Lys
225                 230                 235                 240

Phe Tyr Phe Glu Val Asn Asp Asp Asn Ser Leu Pro Val Gln Asp Asp
                245                 250                 255

Val Asn Leu Phe Asp Tyr Asn Val Gln Glu Arg Val Asn Asp Phe Val
            260                 265                 270

Ala Ala Ala Leu Ser Gln Ala Asn Ile Thr Arg Thr Asn His Ile Met
        275                 280                 285

Trp Thr Met Gly Thr Asp Phe Lys Tyr Gln Tyr Ala His Thr Trp Phe
    290                 295                 300

Arg Asn Met Asp Lys Phe Ile His Tyr Val Asn Gln Asp Gly Arg Val
305                 310                 315                 320

Asn Ala Leu Tyr Ser Ser Pro Ser Ile Tyr Thr Asp Ala Lys Tyr Ala
                325                 330                 335

Leu Asp Glu Ser Trp Pro Leu Lys Thr Gly Asp Tyr Phe Pro Tyr Ala
            340                 345                 350

Asp Arg Ile Asn Ala Tyr Trp Thr Gly Tyr Phe Thr Ser Arg Pro Ala
        355                 360                 365
```

```
Leu Lys Leu Tyr Val Arg Met Met Ser Gly Tyr Tyr Leu Ala Ala Arg
    370             375                 380

Gln Leu Glu Phe Phe Lys Gly Arg Ser Glu Thr Gly Gly Pro Thr Thr
385             390                 395                 400

Glu Val Leu Ala Asp Ala Leu Ala Ile Ala Gln His His Asp Ala Val
                405                 410                 415

Ser Gly Thr Ser Lys Gln His Val Ala Asp Tyr Ala Lys Arg Leu
                420                 425                 430

Phe Ile Gly Tyr Lys Gln Ala Glu Asp Ile Val Ser Asn Ser Leu Ala
            435                 440                 445

Cys Met Val Glu Pro Ala Ser Ala Ser Gly Cys Lys Asn Pro Arg Ile
450                 455                 460

Asn Phe Lys Gln Cys Pro Leu Leu Asn Ile Ser Tyr Cys Pro Pro Thr
465                 470                 475                 480

Glu Ala Asp Leu Ala Pro Gly Lys Lys Leu Val Val Val Tyr Asn
                485                 490                 495

Ala Leu Gly Trp Lys Arg Thr Asp Val Val Arg Ile Pro Val Val Asn
                500                 505                 510

Lys Asn Val Ile Ile Gln Asp Ser Thr Gly Lys Glu Ile Glu Ser Gln
            515                 520                 525

Leu Leu Pro Ile Val Lys Ala Ser Ile Ala Ile Arg Asn Tyr Tyr Ala
            530                 535                 540

Thr Ala Tyr Val Gly Glu Ser Pro Thr Ser Ser Pro Arg Tyr Trp Leu
545                 550                 555                 560

Val Phe Thr Ala Thr Val Pro Pro Leu Gly Phe Asn Ser Tyr Ile Ile
                565                 570                 575

Ser Ser Gly Lys Gln Ala Val Ala Ala Ser Ile Pro Gln Ser Phe Tyr
            580                 585                 590

Lys Thr Asp Gly Ser Gln Ser Asp Val Ile Glu Val Gly Pro Gly Asn
            595                 600                 605

Leu Lys Leu Leu Tyr Ser Ala Asn Gly Gly Lys Phe Thr Gln Tyr Phe
            610                 615                 620

Asn Lys Arg Asn Gln Val Arg Ser Ser Leu Glu Gln Ser Phe Ser Tyr
625                 630                 635                 640

Tyr Ser Ala Asp Asp Gly Ser Lys Asp Ala Tyr Lys Asp Ile Gln Ala
                645                 650                 655

Ser Gly Ala Tyr Val Phe Arg Pro Asn Gly Ser Phe Pro Ile His Pro
            660                 665                 670

Glu Gly Lys Val Pro Ala Thr Ile Leu Arg Gly Pro Leu Leu Asp Glu
            675                 680                 685

Val His Glu Asn Ile Asn Ser Trp Ile Tyr Gln Ile Thr Arg Val Tyr
    690                 695                 700

Lys Glu Lys Glu His Val Glu Val Glu Phe Thr Val Gly Pro Ile Pro
705                 710                 715                 720

Ile Asp Asn Gly Ile Gly Lys Glu Leu Val Thr Gln Ile Gln Thr Asp
                725                 730                 735

Ile Lys Ser Asn Lys Thr Phe Tyr Thr Asp Ser Asn Gly Arg Asp Phe
                740                 745                 750

Leu Lys Arg Ile Arg Asp Tyr Arg Ala Asp Trp Asp Leu Gln Val Asn
            755                 760                 765

Gln Pro Ala Ala Gly Asn Tyr Tyr Pro Ile Asn Leu Gly Ile Phe Leu
770                 775                 780
```

-continued

Lys Asp Asp Ser Asn Glu Phe Ser Val Leu Val Asp Arg Ser Val Gly
785                 790                 795                 800

Gly Ser Ser Leu Val Asp Gly Gln Leu Glu Leu Met Leu His Arg Arg
            805                 810                 815

Leu Leu His Asp Asp Gly Arg Gly Val Ala Glu Ala Leu Asn Glu Thr
        820                 825                 830

Val Cys Ala Leu Gly Lys Cys Met Gly Leu Thr Val Gln Gly Lys Tyr
    835                 840                 845

Tyr Ile Arg Ile Asp Ser Leu Gly Glu Gly Ala Lys Trp Arg Arg Ser
850                 855                 860

Phe Gly Gln Glu Ile Tyr Ser Pro Leu Leu Ala Phe Thr Glu Gln
865                 870                 875                 880

Asp Gly Asp Lys Phe Thr Lys Phe Pro Val Pro Thr Phe Thr Trp Ile
            885                 890                 895

Asp Pro Ser Tyr Ser Leu Pro Asp Asn Val Ala Ile Ile Thr Leu Gln
        900                 905                 910

Glu Leu Glu Asp His Thr Val Leu Leu Arg Leu Ala His Leu Tyr Glu
    915                 920                 925

Val Asp Glu Asp Lys Asp Leu Ser Thr Lys Ala Ile Val Glu Leu Lys
930                 935                 940

Arg Leu Phe Pro Lys Arg Lys Ile Asn Lys Ile Lys Glu Met Ser Leu
945                 950                 955                 960

Ser Ala Asn Gln Glu Arg Glu Met Glu Lys Lys Arg Leu Lys Trp
            965                 970                 975

Lys Ala Glu Ala Pro Ser Asp Ser Gln Asp Val Pro Arg Gly Gly Pro
        980                 985                 990

Val Asp Pro Thr Lys Leu Val Val Glu Leu Ala Pro Met Glu Ile Arg
        995             1000                1005

Thr Phe Val Ile Asn Leu Gly Gln Ser Ser Pro Ala Pro Gly Gly
    1010                1015                1020

Trp Lys Ser His Met Ser Leu
    1025            1030

<210> SEQ ID NO 5
<211> LENGTH: 25
<212> TYPE: DNA
<213> ORGANISM: Artificial Sequence
<220> FEATURE:
<223> OTHER INFORMATION: Synthetic primer

<400> SEQUENCE: 5
caacatgtkg ctratgatta tgcma                                    25

<210> SEQ ID NO 6
<211> LENGTH: 24
<212> TYPE: DNA
<213> ORGANISM: Artificial Sequence
<220> FEATURE:
<223> OTHER INFORMATION: Synthetic primer

<400> SEQUENCE: 6
tggrcgaaam acatatgctc caga                                     24

<210> SEQ ID NO 7
<211> LENGTH: 35
<212> TYPE: DNA
<213> ORGANISM: Artificial Sequence
<220> FEATURE:
<223> OTHER INFORMATION: Synthetic Primer

<400> SEQUENCE: 7
ccgctcgagc gggtggtatc aaacgcagag tacgc                                       35

<210> SEQ ID NO 8
<211> LENGTH: 32
<212> TYPE: DNA
<213> ORGANISM: Artificial Sequence
<220> FEATURE:
<223> OTHER INFORMATION: Synthetic Primer

<400> SEQUENCE: 8
ggggtacccc gtcccaaaag ggtcgatttg cc                                          32

<210> SEQ ID NO 9
<211> LENGTH: 32
<212> TYPE: DNA
<213> ORGANISM: Artificial Sequence
<220> FEATURE:
<223> OTHER INFORMATION: Synthetic Primer

<400> SEQUENCE: 9
gctctagagc gtggtatcaa cgcagagtac gc                                          32

<210> SEQ ID NO 10
<211> LENGTH: 32
<212> TYPE: DNA
<213> ORGANISM: Artificial Sequence
<220> FEATURE:
<223> OTHER INFORMATION: Synthetic Primer

<400> SEQUENCE: 10
ccatcgatgg gtcccaaaag ggtcgatttg cc                                          32

<210> SEQ ID NO 11
<211> LENGTH: 34
<212> TYPE: DNA
<213> ORGANISM: Artificial Sequence
<220> FEATURE:
<223> OTHER INFORMATION: Synthetic Primer

<400> SEQUENCE: 11
ccgctcgagc ggcttcaccg gaggttactc aatg                                        34

<210> SEQ ID NO 12
<211> LENGTH: 32
<212> TYPE: DNA
<213> ORGANISM: Artificial Sequence
<220> FEATURE:
<223> OTHER INFORMATION: Synthetic Primer

<400> SEQUENCE: 12
ggggtacccc gacgtcttga cgattcggat tg                                          32

<210> SEQ ID NO 13
<211> LENGTH: 32
<212> TYPE: DNA
<213> ORGANISM: Artificial Sequence
<220> FEATURE:
<223> OTHER INFORMATION: Synthetic Primer

<400> SEQUENCE: 13
gctctagagc cttcaccgga ggttactcaa tg                                          32

<210> SEQ ID NO 14

```
<211> LENGTH: 32
<212> TYPE: DNA
<213> ORGANISM: Artificial Sequence
<220> FEATURE:
<223> OTHER INFORMATION: Synthetic Primer

<400> SEQUENCE: 14
ccatcgatgg gacgtcttga cgattcggat tg                                      32

<210> SEQ ID NO 15
<211> LENGTH: 20
<212> TYPE: DNA
<213> ORGANISM: Artificial Sequence
<220> FEATURE:
<223> OTHER INFORMATION: Synthetic Primer

<400> SEQUENCE: 15
gttgctgctt caataccaca                                                    20

<210> SEQ ID NO 16
<211> LENGTH: 21
<212> TYPE: DNA
<213> ORGANISM: Artificial Sequence
<220> FEATURE:
<223> OTHER INFORMATION: Synthetic Primer

<400> SEQUENCE: 16
ctccaaagag cttctaacct g                                                  21

<210> SEQ ID NO 17
<211> LENGTH: 20
<212> TYPE: DNA
<213> ORGANISM: Artificial Sequence
<220> FEATURE:
<223> OTHER INFORMATION: Synthetic Primer

<400> SEQUENCE: 17
ttatcaccat tggtgctgag                                                    20

<210> SEQ ID NO 18
<211> LENGTH: 22
<212> TYPE: DNA
<213> ORGANISM: Artificial Sequence
<220> FEATURE:
<223> OTHER INFORMATION: Synthetic Primer

<400> SEQUENCE: 18
cgatgtttcc atacagatcc tt                                                 22
```

POLYNUCLEOTIDE SEQUENCE OF FRUIT SOFTENING ASSOCIATED A-MANNOSIDASE AND ITS USES FOR ENHANCING FRUIT SHELF LIFE

This application is the U.S. National Stage of International Application No. PCT/IN2009/000387, incorporated by reference, filed Jul. 9, 2009, which claims the priority benefit of Indian Application No. 1647/DEL/2008, filed Jul. 9, 2008.

FIELD OF INVENTION

The present invention relates to polynucleotides encoding α-mannosidase of tomato (*Solanum lycopersicum*) and capsicum (*Capsicum annuum*).

BACKGROUND OF THE INVENTION

In today's world of global distribution, the control of fruit ripening is of strategic importance (Causier B, Kieffer M and Davies B, 2002, Science 296: 275-276). One of the major factors limiting fruit shelf life and storage is excessive softening. In this regard, attempts to suppress numerous enzymes have met with limited success in extending shelf life or desired reduction in softening. Ripening is a complex process involving major transitions in fruit development and metabolism to attain organoleptic characteristics to be consumed. Among these, texture is the principal quality attribute for palatability, consumer acceptability, shelf life, transport capability and postharvest disease/pathogen resistance, all of which directly affects the costs. It has been considered axiomatic that these textural changes result primarily from changes in cell wall structure. Cell wall is a dynamic component which mainly consists of carbohydrates and proteins encoded by multigene families. These cell wall polysaccharides are the most abundant organic compounds found in nature whose structural and functional diversity is mirrored by a vast array of enzymes involved in their synthesis (glycosyltransferases), modification (carbohydrate esterases) and breakdown (glycoside hydrolases and polysaccharide lyases). Approximately 1-2% of the organism's genes are involved in these processes, which reveals their importance in fruit ripening (Henrissat B, Coutinho P M and Davies G J, 2001, Plant Mol Biol 47: 55-72 and Jamet E, Canut H, Boudart G and Pont-Lezica R F, 2006, Trends Plant Sci 11: 33-39). Generally, reduction in the fruit firmness is accompanied by the increased expression of numerous cell wall degrading enzymes, like polysaccharide hydrolases/glycoside hydrolase, transglycosylases, lyases and expansins (Brummell D A, 2006, Funct Plant Biol 33: 103-119). Although their general catalytic activity can be inferred from sequence, the precise enzymatic function and biological role of most of these proteins are unknown. Among the suite of enzymes involved in carbohydrates metabolism, hydrolases form a major chunk. These hydrolases target N-glycoproteins found in the cell wall or other organelles and degrade the N-glycoconjugates increasing the free N-glycan content. Furthermore, these free N-glycans are known to have biological activity to stimulate ripening in tomato (Priem B, Gitti R, Bush C A and Gross K C, 1993 Plant Physiol 102: 445-458).

SUMMARY OF THE INVENTION

The present invention relates to the purification and characterization of fruit softening associated enzyme α-mannosidase of tomato (*Solanum lycopersicum*) and capsicum (*Capsicum annuum*). The present invention also relates to identification, isolation and cloning of tomato and capsicum α-mannosidase genes. The present invention further relates to transgenic plants, with reduced α-mannosidase protein accumulation, having enhanced fruit shelf life One aspect of the present invention provides an isolated polynucleotide encoding a polypeptide having mannosidase activity, wherein the nucleotide sequence of the polynucleotide encodes a polypeptide having at least about 85% identity with an amino acid sequence as set forth in SEQ ID NO: 2 or SEQ ID NO: 4.

Another aspect of the present invention provides a polypeptide having amino acid sequence as set forth in SEQ ID NO: 2 or SEQ ID NO: 4.

Yet another aspect of the present invention provides an RNAi construct for suppressing expression of mannosidase in a transgenic plant, the construct comprises a sense polynucleotide strand comprising at least 20 contiguous nucleotides from the sequence as set forth in SEQ ID NO: 1 or SEQ ID NO: 4, and an antisense polynucleotide strand that hybridizes to said sense polynucleotide strand, wherein the antisense polynucleotide strand and the sense polynucleotide strand form a duplex.

Yet another aspect of the present invention provides a process for delaying fruit softening in plant, the process comprising transforming a plant cell, tissue or any part thereof with the recombinant vector comprising the polynucleotide encoding a polypeptide having mannosidase activity, wherein the nucleotide sequence of the polynucleotide encodes a polypeptide having at least about 85% identity with an amino acid sequence as set forth in SEQ ID NO: 2 or SEQ ID NO: 4, wherein the polynucleotide is in anti-sense orientation.

Yet another aspect of the present invention provides a process for delaying fruit softening in plant, the process comprising decreasing the level of mannosidase in transgenic plant compared to its level in non-transgenic plant by expression of an RNA interference (RNAi) construct comprising at least a fragment of at least 20 contiguous nucleotides of the polynucleotide encoding a polypeptide having mannosidase activity, wherein the nucleotide sequence of the polynucleotide encodes a polypeptide having at least about 85% identity with an amino acid sequence as set forth in SEQ ID NO: 2 or SEQ ID NO: 4; and screening the resulting plants for reduced level of mannosidase relative to the non-transgenic plant.

Yet another aspect of the present invention provides a process for delaying fruit softening in plant, the process comprising decreasing the level of mannosidase in transgenic plant compared to its level in non-transgenic plant by expression of an RNA interference (RNAi) construct comprising a sense polynucleotide strand comprising at least 20 contiguous nucleotides from the sequence as set forth in SEQ ID NO: 1 or SEQ ID NO: 3, and an antisense polynucleotide strand that hybridizes to the sense polynucleotide strand, wherein the antisense polynucleotide strand and the sense polynucleotide strand form a duplex; and screening the resulting plants for reduced level of mannosidase relative to the non-transgenic plant.

Yet another aspect of the present invention provides a transgenic plant, seed and progeny thereof comprising the polynucleotide encoding mannosidase, wherein expression of the mannosidase in the plant is controlled to delay fruit softening.

The transgenic plant as disclosed in the present invention encompasses tomato, capsicum, papaya, mango, banana, peach, pear, citrus, pineapple, guava, avocado, strawberry, apple and pomegranate.

BRIEF DESCRIPTION OF ACCOMPANYING DRAWINGS

The above and other features, aspects, and advantages of the subject matter will become better understood with regard to the following description, accompanying drawings and appended claims.

FIG. 1 shows
a) graph showing specific activity of α-mannosidase in tomato fruits at different stages of ripening
b) purified α-mannosidase separated on 6% native gel
c) purified protein denatured and separated on 12.5% SDS-PAGE
d) α-mannosidase protein focused on 4-7 IPG strips in the first dimension and resolved on 12.5% SDS-PAGE in the second dimension
e) EndoH digestion of the purified protein (PP+EndoH) showing a shift as compared to undigested (PP) and detected by α-mannosidase specific antibody.
f) immunoblot analysis of α-mannosidase at different stages of ripening: G-Green, B-Breaker, P-Pink and R-Red Ripe)
g) subcellular localization of α-mannosidase in tomato fruit
h) HPAE chromatograms for three N-linked oligosaccharides on incubating with α-mannosidase.

Figure 2:
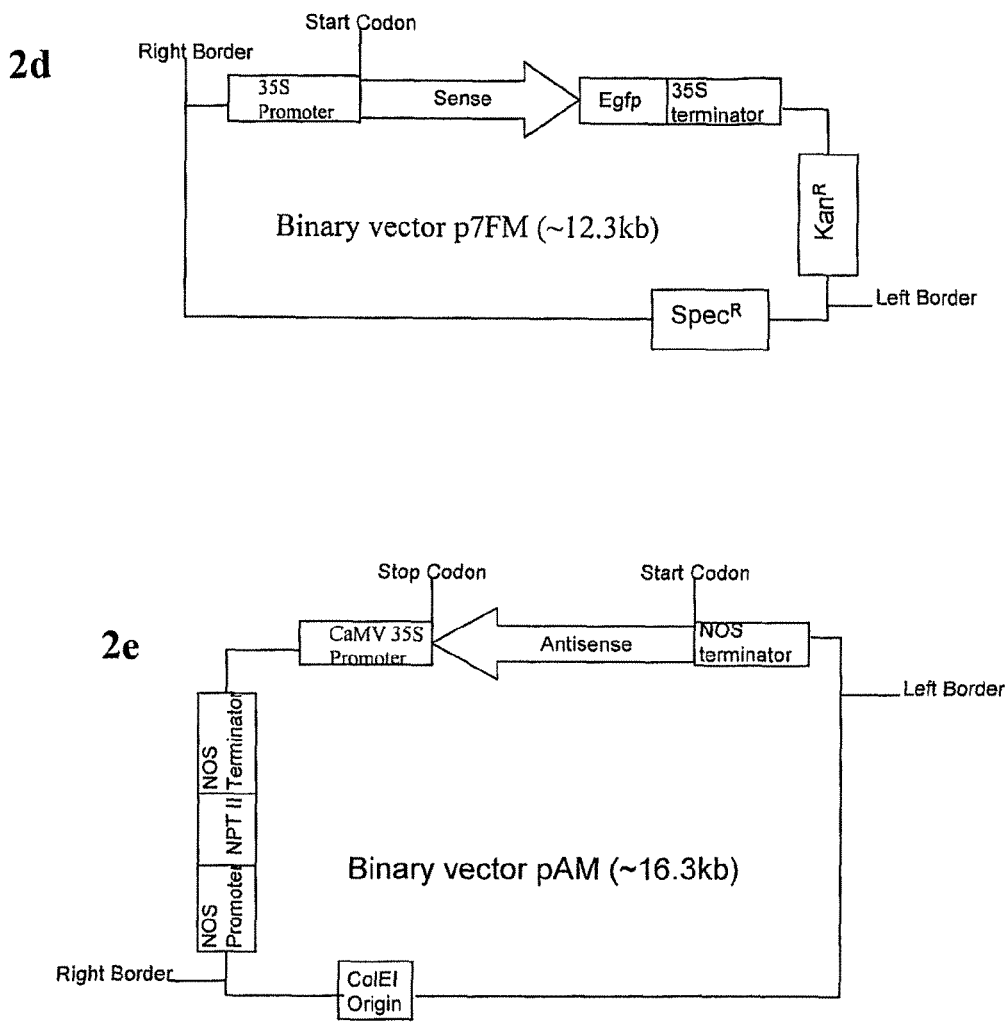
Figure 3:
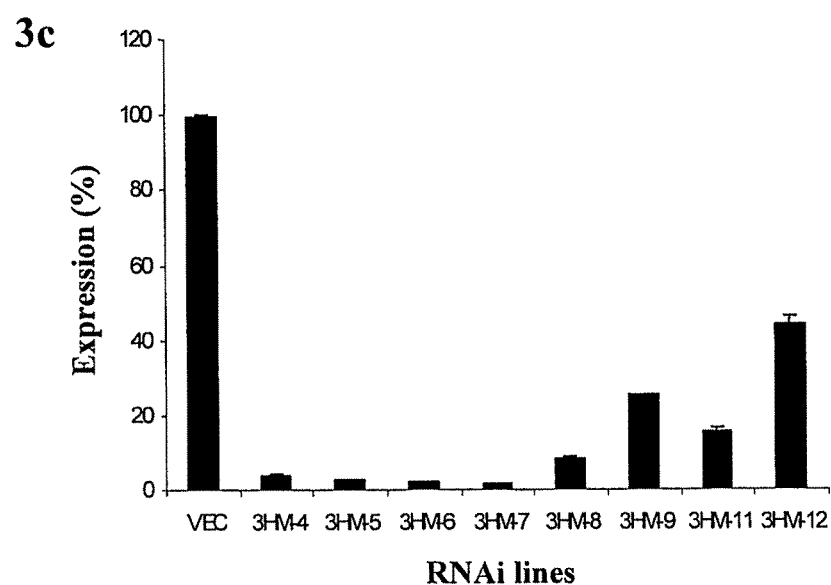

FIG. 2 shows
a) expression of α-mannosidase gene at different stages of ripening in tomato using northern blot analysis
b) RT-PCR analysis showing relative expression of α-mannosidase in ripening impaired mutants rin, nor and Nr as compared to wild type
c) schematic representation of recombinant vector p5HM/p3HM
d) schematic representation of recombinant vector p7FM
e) schematic representation of recombinant vector pAM FIG. 3 shows
a) tomato fruit agroinjected with silencing vector, blank binary vector and overexpression vector.
b) time lapse photography showing representative agroinjected tomato fruits
c) expression analysis of RNAi transgenic lines by RT-PCR to determine the reduction in mannosidase transcript level. Data are mean±SE (n=3)

Figure 4:
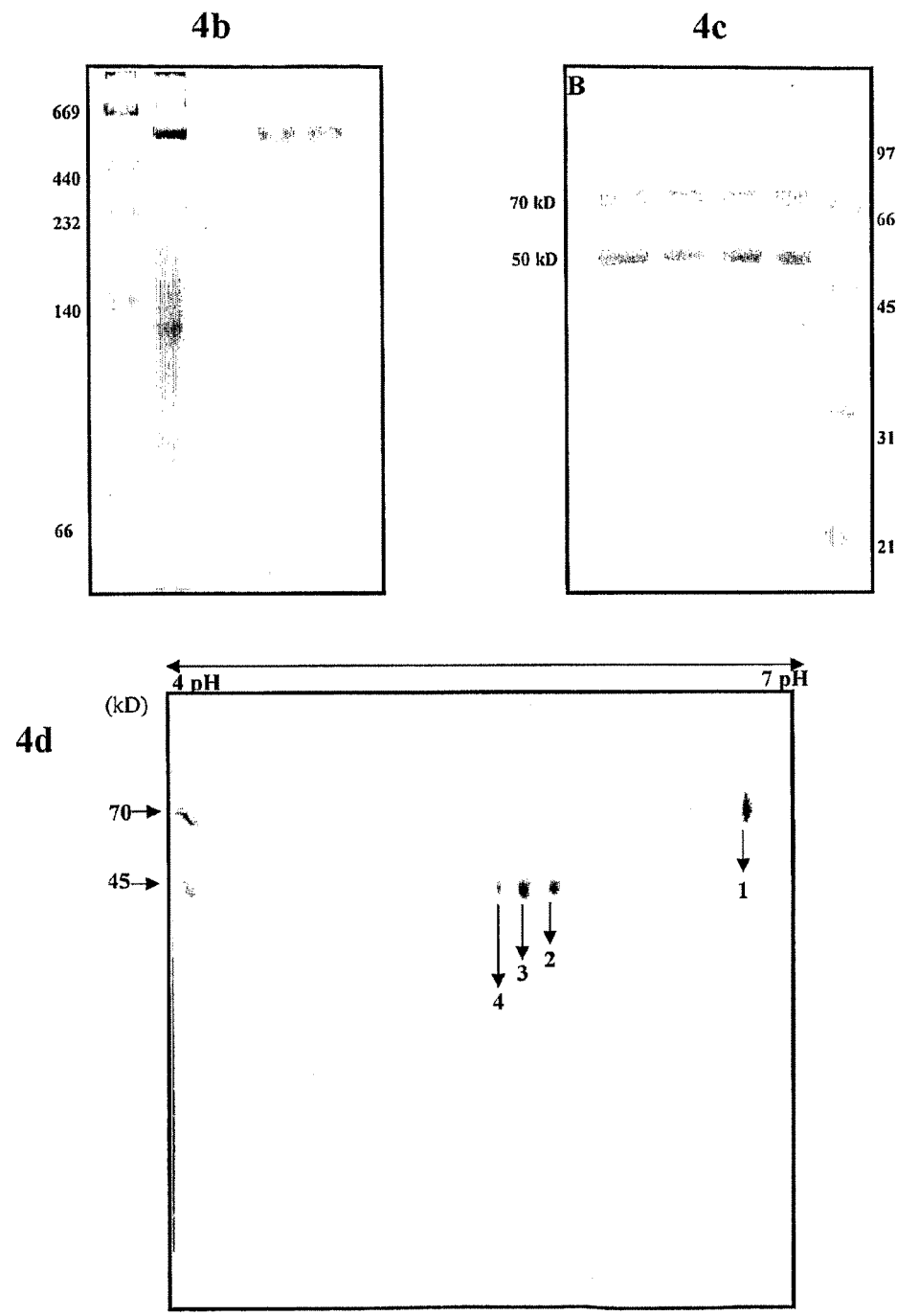

FIG. 4 shows
a) stage wise specific activity of α-mannosidase in capsicum
b) purified α-mannosidase separated on 6% native gel
c) purified protein denatured and separated on 12.5% SDS-PAGE
d) α-mannosidase protein focused on 4-7 IPG strips in the first dimension and resolved on 12.5% SDS-PAGE in the second dimension

DETAILED DESCRIPTION OF THE INVENTION

The present invention relates to tomato and capsicum fruit softening associated α-mannosidase. The instant invention particularly relates to polynucleotide sequences coding for polypeptide having α-mannosidase activity, wherein RNAi and antisense mediated silencing of α-mannosidase in plants delays fruit softening and over expression enhances fruit softening.

The instant invention provides the DNA construct, recombinant vectors and recombinant host cells comprising the polynucleotide coding for the polypeptide having the α-mannosidase activity. The instant invention further provides a method for delaying fruit softening in plants using the polynucleotide of α-mannosidase disclosed in the present invention. The instant invention further provides a method for early fruit softening in plants using the polynucleotide disclosed in the present invention. In addition the instant invention provides the transgenic plants, progeny and seed thereof, wherein expression of α-mannosidase in the plant is controlled to affect fruit softening.

The resultant transgenic plant obtained by the suppressing the expression/β-D-N-acetylmannosidase gene using the antisense and RNAi technology produced fruits which were about 1.5 to 2.5 times firmer than the non transgenic fruits. Moreover the transgenic fruits produced by RNAi technology showed no signs of softening up to 45 days of harvest which is almost 30 days more than the non-transgenic fruits. The transgenic fruits produced by the antisense technology showed no signs of softening up to 35 days of harvest which is almost 20 days more than the non-transgenic fruits. These results are surprising and unexpected. Further suppression of the gene in transgenic plants had no negative effect on vegetative growth, flowering and fruit development, days to maturity and yield.

The present invention describes the method to enhance tomato shelf life by suppressing a glycosyl hydrolase family gene, α-mannosidase, by RNA interference (RNAi) technology, which is responsible for carbohydrate metabolism and N-glycan processing in plants. The present invention further describes purification and characterization of the α-mannosidase protein complex from the tomato pericarp.

The LC MS/MS analysis of 2DE focused protein complex helped in identification of the interacting partners and also in cloning the α-mannosidase gene. The expression of α-mannosidase gene was highest during breaker stage and correlated with initiation of ripening/softening. Molecular analysis of transgenic fruits indicated that α-mannosidase transcript was specifically degraded up to 99% resulting up to 2.5 times firmer fruits with 30 days of enhanced shelf life. In the course of the study we found that mannosidase was induced by geraniol, a terpeniod present in the plants, and regulated by rin.

Using pNP-alpha-D-mannopyrinoside as substrate we found maximum activity of mannosidase at breaker (FIG. 1a) followed by green, pink and red stages of ripening. Accumulation of α-mannosidase at breaker stage, which marks the beginning of process like respiration or ethylene production, accumulation of carotenoides and softening strengthened our hypothesis of it being involved in ripening and/or softening.

The tomato α-mannosidase was purified from the pericarp of the breaker stage tomato and further characterized. The tomato pericarp was crushed in liquid nitrogen and suspended overnight in extraction buffer (100 mM Tris-Cl, pH 7.8 with 0.25 NaCl with 1 mM PMSF) Methods like ammonium sulphate precipitation (0-70%), ion exchange (DEAE sepharose) and gel filtration chromatography (Sephadex G-100) were employed to purify the protein to homogeneity. The purified enzyme constituted a single protein of 360 kD on 6% native PAGE (FIG. 1b) which was confirmed by α-mannosidase activity-band correlation. However, on the contrary the molecular weight of the protein as determined by gel filtration using superdex 200 analytical column was 290 kD. Further, when separated on SDS-PAGE the protein resolved in to two subunits of 70 kD and 4510 revealing it to be a heterodimer (FIG. 1c). To obtain a clear picture, the protein complex was separated on 2-Dimensional gel electrophoresis (2DE) which revealed that 70 kD subunit was a single protein and the 45 kD subunit further resolved into three proteins with different pIs (FIG. 1d). We identified the spots by LC/MS-MS analysis and found that each one of them was a different protein. The 70 kD spot represented the α-mannosidase (spot no. 1, pI 6.8) and the 45 kD spot which split into three proteins had putative monosaccharide transporter (spot no. 2, pI 6.4), geraniol responsible factor (spot no. 3, pI 6.3) which is the part of the gene and the H+ATPase (spot no. 4, pI 6.2). Therefore, we predicted that, two of the three proteins found in 45 kD complex may be interacting proteins.

Biochemical characterization revealed that the enzyme was stable upto 60° C. for 1 hr without considerable reduction in the activity. The temperature and pH optimum for the enzyme was 45° C. and pH 6.0, respectively. The determined Km of the enzyme is 4.6 mM for p-Nitrophenol-alpha-D-mannopyrinoside. To identify the nature of the tomato α-mannosidase it was resolved on SDS-PAGE and subjected to PAS staining, the protein stained positive for glycoproteins. To further confirm the above results, EndoH digestion of the protein was performed which showed a shift of 2-3 kD due to cleavage of carbohydrate/glycan moiety, validating the above results (FIG. 1e). In order to correlate specific activity at particular ripening stage with the protein accumulation, immunoblot analysis of all the stages was done using polyclonal antibody raised against 70 kD subunit of the protein homologus to α-mannosidase. Immunoblot analysis revealed maximum protein accumulation at breaker stage followed by green, pink and red (FIG. 1f). Furthermore, to determine its distribution in the cell, immunolocalization assay was done, which revealed it to be a cell wall protein as the signal was seen at the extreme inner edge of the cell wall (FIG. 1g). Our finding was further reinforced by a report in Arabidopsis which classified α-mannosidase homologue (Q8LPJ3) into cell wall protein with a signal peptide for secretion. To decipher the role of α-mannosidase on N-glycans and their processing, we targeted three N-linked oligosaccharides (Oligomannose-3, Oligomannose-5 and Oligomannose-9) commonly found in the fruit pericarp. To verify its action on N-glycans, α-mannosidase was incubated with N-linked oligosaccharides at 37° C. overnight and the reaction mixture was resolved on Carbopac PA-1 column. The enzyme was able to cleave terminal mannose residue/s from all the N-linked oligosaccharides giving an indirect evidence of it being involved in ripening/softening (FIG. 1h).

The cDNA was amplified using degenerate primers corresponding to the peptide QHVADDYAK and SGAYVFRP wherein the oligonucleotide sequence of the primers are as set forth in SEQ ID NO: 5 and SEQ ID NO: 6. The primers were designed using the LC-MS/MS data and motifs identified by multiple alignment. The missing portions of 5' and 3' ends were amplified and made to full length by Random Amplification of cDNA Ends (RACE). In-silico analysis of the sequence revealed the coding region to be 3090 bp long (SEQ ID NO: 1) and the deduced protein was 1029 amino acid long (SEQ ID NO: 2) with calculated mass and theoretical pI of 114 KDa and 6.48, respectively. The tomato α-mannosidase protein showed 66% and 62% identity with Arabidopsis and rice α-mannosidase protein, respectively. To gain insight into its evolutionary aspect phylogenetic analysis was performed which showed that α-mannosidase is most closely related to two of the three known Arabidopsis α-mannosidase proteins. To verify the expression pattern and corroborate the earlier results, northern blot analysis was performed which revealed that mannosidase transcript are most abundant in breaker followed by green, pink and red stage (FIG. 2a).

```
Left primer:
5' CAACATGTKGCTRATGATTATGCMA    SEQ ID NO: 5 right primer:
5' TGGRCGAAAMACATATGCTCCAGA     SEQ ID NO: 6
```

Wherein K is G or T, R is A or G, and M is A or C

The expression of the α-mannosidase was analyzed in tomato mutant rin (ripening inhibitor), nor and Nr. The analysis revealed that the α-mannosidase was inhibited up to 90% in mutant rin, 30% in Nr, while nor mutant was comparable to the wild type (FIG. 2b). Further analysis of the mutant was carried out, which carries a mutation in a gene encoding a MADS-box transcription factor, required for developmental regulation of fruit ripening. We used ACC, the precursor of ethylene, to induce mannosidase in rin mutant as well as in wild type. ACC was able to up regulate the α-mannosidse in both rin as well as wild type compared to the control. These observations showed that α-mannosidsae is regulated by ethylene as well as rin independently or synergistically.

Backed by many observations, functional characterization of α-mannosidase became imperative, by silencing, to demonstrate its role in ripening and/or associated softening. Endogene supression using agroinjection has become a handy tool for analyzing the gene function (Orzaez D F, Mirabel S, Wieland W H and Granell A, 2006, Plant Physiol 140: 3-11). Using this dsRNA mediated silencing technique we transiently silenced the α-mannosidase using pHANNIBAL vector (Wesley S V, Helliwell C A, Smith N A, Wang M B, Rouse D T, Liu Q, Gooding P S, Singh S P, Abbott D, Stoutjesdijk P A, Robinson S P, Gleave A P, Green A G and Waterhouse P M, 2001, Plant J 27: 581-590). The expression cassette consisted of 600 bp fragment of the gene from either 5' or 3' region including respective UTR regions sub cloned in sense and antisense orientation separated by an intron under the control of CaMV 35S promoter designed to assemble into dsRNA upon expression. The oligonucleotide sequences of the primers used in the construction of RNAi cassette are as set forth in SEQ ID NO:7, SEQ ID NO:8, SEQ ID NO:9, SEQ ID NO:10, SEQ ID NO:11, SEQ ID NO:12, SEQ ID NO:13 and SEQ ID NO:14. This cassette was further subcloned into binary vector pART 27 and designated the binary vector as p5HM/p3HM (FIG. 2c). Each fruit was injected at 2-3 spots on the surface near the stylar apex (FIG. 3a) depending upon its size. After a week the RNAi agroinjected fruits developed prominent green sectors around the injected spot covering the maximum area around the fruit compared to that of control (Blank binary vector) (FIG. 3a). To confirm and quantitate suppression at molecular level, fruits harvested after 2-4 days of injection were used to determine the reduction in mRNA level corresponding to α-mannosidase by real Time RT-PCR. The oligonucleotide primers were designed using light cycler probe design 2 program (Roche). The oligonucleotide sequences of the primers used in the amplification α-mannosidase are as set forth in SEQ ID NO: 15 and SEQ ID NO: 16. Primers used for endogenous control gene, actin amplification are set forth in SEQ ID NO: 17 and SEQ ID NO: 18.

```
                                              SEQ ID NO: 7
5' CCGCTCGAGCGGGTGGTATCAAACGCAGAGTACGC 3'

SEQ ID NO: 8
5' GGGGTACCCCGTCCCAAAAGGGTCGATTTGCC 3'

SEQ ID NO: 9
5' GCTCTAGAGCGTGGTATCAACGCAGAGTACGC 3'
```

-continued

SEQ ID NO: 10
5' CCATCGATGGGTCCCAAAAGGGTCGATTTGCC 3'

SEQ ID NO: 11
5' CCG CTCGAGCGGCTTCACCGGAGGTTACTCAATG 3'

SEQ ID NO: 12
5' GGGGTACCCCGACGTCTTGACGATTCGGATTG 3'

SEQ ID NO: 13
5' GCTCTAGAGCCTTCACCGGAGGTTACTCAATG 3'

SEQ ID NO: 14
5' CCATCGATGGGACGTCTTGACGATTCGGATTG 3'

SEQ ID NO: 15
5'GTTGCTGCTTCAATACCACA3'

SEQ ID NO: 16
5' CTCCAAAGAGCTTCTAACCTG3'

SEQ ID NO: 17
5'TTATCACCATTGGTGCTGAG3'

SEQ ID NO: 18
5' CGATGTTTCCATACAGATCCTT 3'

The results reveled that the mRNA level was reduced up to 70% when injected 2 days before green stage and up to 50% when injected at green stage relative to the control. To validate the results, overexpression construct of α-mannosidase prepared in pK7FWG 2.0 and designated as p7FM (FIG. 2d) was agroinjected into the fruits which behaved similar to the control during early stages. The effect of over expression was seen at later stages, as the fruits deteriorated and lost their texture much quicker than the control (Blank vector and Uninjected). Antisense construct was also prepared in pBI121 designated as pAM, (FIG. 2e) to see its effect. The antisense injected fruits were intermediate to overexpression and silenced fruits. This reduction in mRNA level prompted us to explore the presence of 21-23 mer small molecular weight RNAs (siRNA). For this purpose, we extracted soluble small RNAs from green and breaker stage fruits of RNAi along with control and performed northern blot analysis. We observed small interfering (si) RNAs in the fruit pericarps specific to α-mannosidase which are the hallmark of RNAi mediated silencing. Additionally, our results also demonstrate that non viral vectors could perform silencing with same efficiency and magnitude as the viral vectors.

In an attempt to quantify the texture firmness of agroinjected fruits after 30 days of agroinjection, compression analysis using TA-XT2 texture analyzer was performed. As ripening is not a uniform process the fruit firmness was measured by compressing the fruits through 5 mm at different planes of the fruit (2-3 compressions/fruit) and single 10 mm compression with stylar end touching the plate of the texture analyzer. In all the cases, RNAi agro injected fruits were statistically firmer and were 2 and 1.6 times firmer than their counterpart in 5 mm and 10 mm compressions, respectively. Further, time lapse photography of the agroinjected fruits revealed that the RNAi injected fruits retained their texture and firmness up to 45 days, compared to the control which started shrinking and loosing their texture after 15 days (FIG. 3b). These encouraging results prompted us to raise stable RNAi lines using the same vector. The Agrobacterium mediated transformation of tomato cotyledons resulted in RNAi lines expressing sense and antisense fragment of the gene separated by an intron. The cotyledon leaves were co-cutivated with agro bacterium strain EHA105 transformed with silencing vector and selected on kanamycin plates. Other than the strains used in this study, strains like LBA 4404 and GV 3101 can also be employed to get the same effect. The explants were subcultured every 12-15 days until shoots appeared. When the shoots were 1-2 cm long they were cut and grown in rooting media. The putative silenced plants ($T_0$) were investigated for reduction in transcript level by real time RT-PCR, which revealed that α-mannosidase was suppressed up to 99% at breaker stage (FIG. 3c). The fruits were then harvested at pink stage and stored at room temperature for texture analysis. The transgenic fruit produced by Antisense technology showed upto 80% suppression of mannosidase and upto 1.5 times firmness as compared to the non-transgenic fruits. After 30 days, RNAi fruits were observed to be 2.5 times firmer than the control without any negative effects on growth, development and seed production. The transgenic fruits produced by the antisense technology showed upto 20 days enhancement of shelf life.

Capsicum being non climacteric fruit, fruit development and ripening was divided into 8 stages. Taking matured fruits from stage 8, protein extraction was done in Tris-Cl pH 7. Activity assay was performed at all the different stages of development and ripening of capsicum and maximum activity was found in stage 8 fruits (FIG. 4a). The capsicum mannosidase was purified by employing different chromatographic techniques like ion exchange and gel filtration. The eluted fractions containing the activity were concentrated and resolved on the gel. The purified protein was a single band of ~500 kD on 6% native gel (FIG. 4b) and on SDS-PAGE two subunits of 70 and 50 kD were resolved (FIG. 4c). Electrofocusing of purified protein on 2DE revealed it to be a complex and gave a hint of interacting proteins. The lower 50 kD band separated into three proteins with different pIs very much similar to tomato mannosidase (FIG. 4d). Immunolocalisation revealed that it is localized in the cell wall. The capsicum α-mannosidase was 90% identical to tomato α-mannosidase. Molecular cloning of α-mannosidase from capsicum revealed that the coding region was 3093 bp long (SEQ ID NO: 3). The deduced protein from capsicum was 1030 amino acid long (SEQ ID NO: 4). Transient silencing of α-mannosidase by agroinjection in capsicum revealed that it is involved in ripening associated softening.

Geraniol is an acyclic dietary monoterpene, having in vitro and in vivo antitumor activity against various cancer cell lines and is therefore considered as a new class of agents for cancer chemoprevention. It was also reported that geraniol interferes with the membrane functions of Candida albicans and Saccharomyces cervisiae. As geraniol is not soluble in water, 20% DMSO was used to feed the seedlings (Hendry GAF and Jones OTG, 1984, Induction of cytochrome p-450 in intact mung beans. New Phytol 96: 153-159). We observed an up-regulation up to 3 fold in mannosidase gene expression after 30 min of geraniol treatment compared to control (DMSO only). This instigated us to further analyze the role of geraniol on α-mannosidase induction in pleiotropic rin mutant. The rin seedlings were fed with 10% geraniol and samples collected. Relative gene expression analysis revealed that α-mannosidase transcript was up regulated up to 6 fold after 30 min substantiating the earlier results.

One embodiment of the present invention provides an isolated polynucleotide coding for a polypeptide having α-mannosidase activity, wherein the nucleotide sequence of said polynucleotide is selected from the group consisting of
   a. a nucleotide sequence coding for a polypeptide having 90% similarity to an amino acid sequence as set forth in SEQ ID NO: 2;
   b. a nucleotide sequence coding for a polypeptide having 90% identity with an amino acid sequence as set forth in SEQ ID NO: 4;

c. a nucleotide sequence complementary to said nucleotide sequence of a) or b)
d. a nucleotide sequence as set forth in SEQ ID NO: 1;
e. a nucleotide sequence as set forth in SEQ ID NO: 3;
f. a nucleotide sequence complementary to said nucleotide sequence of d), or e).

Another embodiment of the present invention provides the polynucleotide coding for a polypeptide having α-mannosidase activity disclosed in the present invention is isolated from tomato, wherein the nucleotide sequence is as set forth in SEQ ID NO: 1.

Yet another embodiment of the present invention provides the polynucleotide coding for a polypeptide having α-mannosidase activity disclosed in the present invention is isolated from capsicum, wherein the nucleotide sequence is as set forth in SEQ ID NO: 3.

One embodiment of the present invention provides an isolated polynucleotide having nucleotide sequence as set forth in SEQ ID NO: 1 and SEQ ID NO: 3.

Further embodiment of the present invention provide the polypeptide having α-mannosidase activity having amino acid sequence as set forth in SEQ ID NO: 2 and SEQ ID NO: 4.

Still yet another embodiment of the present invention provides a DNA construct comprising the polynucleotide coding for a polypeptide having α-mannosidase activity disclosed in the present invention, wherein the polynucleotide sequence is operable linked to a promoter sequence.

Further embodiment of the present invention provides the DNA construct of the present invention, wherein part of the polynucleotide sequence is in sense and antisense orientation separed by an intron.

Still yet another embodiment of the present invention provides a DNA construct comprising part of the polynucleotide having nucleotide sequence as set forth in SEQ ID NO: 1 coding for a polypeptide having α-mannosidase activity, wherein the polynucleotide sequence is in sense and antisense direction separated by an intron.

Still yet another embodiment of the present invention provides a DNA construct comprising part of the polynucleotide having nucleotide sequence as set forth in SEQ ID NO: 3 coding for a polypeptide having α-mannosidase activity, wherein the polynucleotide sequence is in sense and antisense direction separated by an intron.

The present invention also provides a recombinant vector comprising the DNA construct disclosed in the present invention.

The present invention further provides a recombinant vector comprising part of the polynucleotide having nucleotide sequence as set forth in SEQ ID NO: 1 coding for a polypeptide having α-mannosidase activity, wherein the polynucleotide sequence is in sense and antisense direction separated by an intron.

The present invention further provides a recombinant vector comprising part of the polynucleotide having nucleotide sequence as set forth in SEQ ID NO: 3 coding for a polypeptide having α-mannosidase activity, wherein the polynucleotide sequence is in sense and antisense direction separated by an intron.

In one embodiment, the present invention provides a recombinant host cell comprising the vector disclosed in the present invention.

In one embodiment, the present invention provides a recombinant host cell comprising part of the polynucleotide having nucleotide sequence as set forth in SEQ ID NO: 1 coding for a polypeptide having α-mannosidase activity, wherein the polynucleotide sequence is in sense and antisense direction separated by an intron.

In one embodiment, the present invention provides a recombinant host cell comprising part of the polynucleotide having nucleotide sequence as set forth in SEQ ID NO: 3 coding for a polypeptide having mannosidase activity, wherein the polynucleotide sequence is in sense and antisense direction separated by an intron.

In another embodiment, relates to host cells selected from the group consisting of *Agrobacterium, E. coli* and yeast.

In another embodiment, the present invention provides a process for delaying fruit softening in plant, the method comprising transforming a plant cell, tissue or any part thereof with the recombinant vector of the present invention, wherein said vector comprises part of the polynucleotide coding for a polypeptide having α-mannosidase activity is in sense and antisense direction separated by an intron.

In another embodiment, the present invention provides a process for delaying fruit softening in plant, the method comprising transforming a plant cell, tissue or any part thereof with the recombinant vector of the present invention, wherein said vector comprises the polynucleotide coding for a polypeptide having α-mannosidase activity is in antisense direction.

In another embodiment, the present invention provides a process for early fruit softening in plant, said method comprising transforming a plant cell, tissue or any part thereof with the recombinant vector of the present invention, wherein said vector comprises the polynucleotide coding for a polypeptide having α-mannosidase activity is in sense direction.

In another embodiment, the present invention provides a process for delaying fruit softening in plant, the method comprising transforming a plant cell, tissue or any part thereof with the recombinant vector of the present invention, wherein said vector comprises the polynucleotide having nucleotide sequence as set forth in SEQ ID NO: 1 coding for a polypeptide having α-mannosidase activity is in antisense direction.

In another embodiment, the present invention provides a process for early fruit softening in plant, the method comprising transforming a plant cell, tissue or any part thereof with the recombinant vector of the present invention, wherein said vector comprises the polynucleotide having nucleotide sequence as set forth in SEQ ID NO: 3 coding for a polypeptide having α-mannosidase activity is in sense direction.

The process for delaying fruit softening or early fruit softening in plant provided in the present invention, wherein the transformation can be carried out by the method known in the art such as *Agrobacterium* mediated transformation, particle gun bombardment, electroporation and in planta transformation.

In one embodiment, the present invention provides a transgenic plant produced by the process disclosed in the present invention, wherein expression of α-mannosidase in said plant is controlled to effect fruit softening eventually leading in fruit ripening, wherein the plant is selected from the group consisting of tomato, capsicum, mango, banana, papaya, citrus, guava, avocado, grapes, pineapple, strawberry, apple, pomegranate and other fruit crop plants.

A transgenic plant produced by the process disclosed in the present invention is tomato.

The present invention also provides a seed or progeny of the transgenic plant disclosed in the present invention.

In one embodiment of the present invention there is provided an isolated polynucleotide coding for a polypeptide having mannosidase activity, wherein the nucleotide sequence of said polynucleotide encodes a polypeptide having at least about 88% identity with an amino acid sequence as set forth in SEQ ID NO: 2 or SEQ ID NO: 4.

In another embodiment of the present invention there is provided an isolated polynucleotide coding for a polypeptide having mannosidase activity, wherein the nucleotide sequence of said polynucleotide encodes a polypeptide having at least about 90% identity with an amino acid sequence as set forth in SEQ ID NO: 2 or SEQ ID NO: 4.

Another embodiment of the present invention provides an RNAi constructs comprising at least 20 contiguous nucleotides from the polynucleotide encoding a polypeptide having mannosidase activity are selected in such a way that these nucleotides form only hairpin structure and do not form secondary loop within its length, wherein the nucleotide sequence of said polynucleotide encodes a polypeptide having at least about 85% identity with an amino acid sequence as set forth in SEQ ID NO: 2 or SEQ ID NO: 4.

Another embodiment of the present invention provides an RNAi constructs comprising at least 20 contiguous nucleotides from the polynucleotide encoding a polypeptide having mannosidase activity are selected in such a way that these nucleotides form only hairpin structure and do not form secondary loop within its length, wherein the nucleotide sequence of said polynucleotide is as set forth in SEQ ID NO: 1 or SEQ ID NO: 3.

The RNAi constructs disclosed in the present invention form hairpin structure after transcription in the plant.

The RNAi constructs disclosed in the present invention is a hairpin nucleic acid.

The RNAi construct disclosed in the present invention form hairpin structure after transcription in the plant, and does not form the secondary loop structure.

Another embodiment provides an RNAi constructs comprising the polynucleotide sequence as disclosed in the present invention form hairpin structure after transcription in the plant.

Yet another aspect of the present invention provides an isolated polynucleotide encoding a polypeptide having mannosidase activity, wherein the nucleotide sequence of the polynucleotide encodes a polypeptide having at least about 85% identity with an amino acid sequence as set forth in SEQ ID NO: 2 or SEQ ID NO: 4.

Yet another aspect of the present invention provides an isolated polynucleotide encoding a polypeptide having mannosidase activity, wherein the nucleotide sequence of the polynucleotide encodes a polypeptide having amino acid sequence as set forth in SEQ ID NO: 2 or SEQ ID NO: 4.

Yet another aspect of the present invention provides an isolated polynucleotide encoding a polypeptide having mannosidase activity, wherein the nucleotide sequence of the polynucleotide is as set forth in SEQ ID NO: 1 or SEQ ID NO: 3.

Yet another embodiment of the present invention provides a polypeptide having amino acid sequence as set forth in SEQ ID NO: 2 or SEQ ID NO: 4.

Yet another aspect of the present invention provides a DNA construct comprising an isolated polynucleotide encoding a polypeptide having mannosidase activity, wherein the nucleotide sequence of the polynucleotide encodes a polypeptide having at least about 85% identity with an amino acid sequence as set forth in SEQ ID NO: 2 or SEQ ID NO: 4, wherein the polynucleotide is operably linked to a promoter sequence.

Yet another aspect of the present invention provides a DNA construct comprising an isolated polynucleotide encoding a polypeptide having mannosidase activity, wherein the nucleotide sequence of the polynucleotide encodes a polypeptide having amino acid sequence as set forth in SEQ ID NO: 2 or SEQ ID NO: 4, wherein the polynucleotide is operably linked to a promoter sequence.

Yet another aspect of the present invention provides a DNA construct comprising an isolated polynucleotide encoding a polypeptide having mannosidase activity, wherein the nucleotide sequence of the polynucleotide is as set forth in SEQ ID NO: 1 or SEQ ID NO: 3, wherein the polynucleotide is operably linked to a promoter sequence.

Yet another aspect of the present invention provides a DNA construct comprising an isolated polynucleotide encoding a polypeptide having mannosidase activity, wherein the nucleotide sequence of the polynucleotide encodes a polypeptide having at least about 85% identity with an amino acid sequence as set forth in SEQ ID NO: 2 or SEQ ID NO: 4, wherein the polynucleotide is operably linked to a promoter sequence, wherein the polynucleotide sequence is in sense orientation.

Yet another aspect of the present invention provides a DNA construct comprising an isolated polynucleotide encoding a polypeptide having mannosidase activity, wherein the nucleotide sequence of the polynucleotide encodes a polypeptide having at least about 85% identity with an amino acid sequence as set forth in SEQ ID NO: 2 or SEQ ID NO: 4, wherein the polynucleotide is operably linked to a promoter sequence, wherein the polynucleotide sequence is in antisense orientation.

Another embodiment of the present invention provides an RNAi construct for suppressing expression of mannosidase in a transgenic plant, the construct comprises a sense polynucleotide strand comprising at least 20 contiguous nucleotides from the sequence as set forth in SEQ ID NO: 1 or SEQ ID NO: 4, and an antisense polynucleotide strand that hybridizes to said sense polynucleotide strand, wherein the antisense polynucleotide strand and the sense polynucleotide strand form a duplex.

The RNAi construct as disclosed in the present invention, wherein the RNAi construct is a hairpin nucleic acid.

The RNAi construct as disclosed in the present invention, wherein the sense strand comprises 100 to 600 nucleotides.

Another embodiment of the present invention provides a recombinant vector comprising the DNA construct as disclosed in the present invention.

Another embodiment of the present invention provides a recombinant host cell selected from the group consisting of *Agrobacterium*, *E. coli* and yeast.

Yet another embodiment of the present invention provides a process for delaying fruit softening in plant, the process comprising transforming a plant cell, tissue or any part thereof with the recombinant vector comprising the polynucleotide encoding a polypeptide having mannosidase activity, wherein the nucleotide sequence of said polynucleotide encodes a polypeptide having at least about 85% identity with an amino acid sequence as set forth in SEQ ID NO: 2 or SEQ ID NO: 4, wherein the polynucleotide is in antisense orientation.

Yet another embodiment of the present invention provides a process for delaying fruit softening in plant, the process comprising transforming a plant cell, tissue or any part thereof with the recombinant vector comprising the polynucleotide encoding a polypeptide having mannosidase activity, wherein the nucleotide sequence of said polynucleotide encodes a polypeptide having at least about 85% identity with an amino acid sequence as set forth in SEQ ID NO: 2 or SEQ ID NO: 4, wherein the polynucleotide is in antisense orientation, wherein the nucleotide sequence of the polynucleotide is as set forth in SEQ ID NO: 1 and SEQ ID NO: 3.

Yet another embodiment of the present invention provides a process for delaying fruit softening in plant, the process comprising decreasing the level of mannosidase in transgenic plant compared to its level in non-transgenic plant by expression of an RNA interference (RNAi) construct comprising at least a fragment of at least 20 contiguous nucleotides of the polynucleotide encoding a polypeptide having mannosidase activity, wherein the nucleotide sequence of the polynucleotide encodes a polypeptide having at least about 85% identity with an amino acid sequence as set forth in SEQ ID NO: 2 or SEQ ID NO: 4; and screening the resulting plants for reduced level of mannosidase relative to the non-transgenic plant.

Yet another embodiment of the present invention provides a process for delaying fruit softening in plant, the process comprising decreasing the level of mannosidase in transgenic plant compared to its level in non-transgenic plant by expression of an RNA interference (RNAi) construct comprising at least a fragment of at least 20 contiguous nucleotides of the polynucleotide encoding a polypeptide having mannosidase activity, wherein the nucleotide sequence of the polynucleotide encodes a polypeptide having at least about 85% identity with an amino acid sequence as set forth in SEQ ID NO: 2 or SEQ ID NO: 4; and screening the resulting plants for reduced level of mannosidase relative to the non-transgenic plant, wherein the nucleotide sequence of the polynucleotide is as set forth in SEQ ID NO: 1 and SEQ ID NO: 3.

Yet another embodiment of the present invention provides a process for delaying fruit softening in plant, the process comprising decreasing the level of mannosidase in transgenic plant compared to its level in non-transgenic plant by expression of an RNA interference (RNAi) construct comprising a sense polynucleotide strand comprising at least 20 contiguous nucleotides from the sequence as set forth in SEQ ID NO: 1 or SEQ ID NO: 3, and an antisense polynucleotide strand that hybridizes to the sense polynucleotide strand, wherein the antisense polynucleotide strand and the sense polynucleotide strand form a duplex; and screening the resulting plants for reduced level of mannosidase relative to the non-transgenic plant.

Yet another embodiment of the present invention provides a process for delaying fruit softening in plant, the process comprising decreasing the level of mannosidase in transgenic plant compared to its level in non-transgenic plant by expression of an RNA interference (RNAi) construct comprising a sense polynucleotide strand comprising at least 20 contiguous nucleotides from the sequence as set forth in SEQ ID NO: 1 or SEQ ID NO: 3, and an antisense polynucleotide strand that hybridizes to the sense polynucleotide strand, wherein the antisense polynucleotide strand and the sense polynucleotide strand form a duplex; and screening the resulting plants for reduced level of mannosidase relative to the non-transgenic plant, wherein the RNAi construct is a hairpin nucleic acid.

Yet another embodiment of the present invention provides a transgenic plant, seed or progeny thereof comprising the polynucleotide encoding mannosidase, wherein expression of the mannosidase in the plant is controlled to delay fruit softening.

The transgenic plant as disclosed in the present invention encompasses tomato, capsicum, papaya, mango, banana, peach, pear, citrus, pineapple, guava, avocado, strawberry, apple and pomegranate.

The transgenic plant as disclosed in the present invention is tomato. The transgenic plant as disclosed in the present invention is capsicum.

EXAMPLE

It should be understood that the following examples described herein are for illustrative purposes only and that various modifications or changes in light will be suggested to persons skilled in the art and are to be included within the spirit and purview of this application and the scope of the appended claims.

Example 1

Purification and Enzyme Assay of α-mannosidase From Tomato

Tomato seeds (cv. Pusa Ruby and the mutants) were germinated in pre-sterilized soil and later the seedlings were transplanted to the greenhouse with ~25° C. temperature, 70% humidity and 14/10 h light/dark regime. For analysis, fruit were harvested at mature green, breaker, pink and red ripe stage after tagging the flowers at anthesis. Mutants used in the study were procured from Tomato Genetics Resource Center (TGRC).

The pericarp was powdered in liquid nitrogen, suspended in one fourth volume of extraction buffer (100 mM Tris-Cl pH 7.8 with 0.25 M NaCl and 1 mM PMSF). The supernatant after centrifugation was subjected to 0-70% ammonium sulphate precipitation and centrifuged at 10,000 g for 10 min. The pellet thus obtained was dialyzed overnight against 25 mM Tris-Cl pH 7.8. The dialysate was chromatographed on DEAE Sepharose pH 7.8 and eluted with increasing salt gradient (Supplementary FIG. 2A-B). The fractions eluted at 100 mM salt concentration were pooled and subjected to 0-80% ammonium sulphate precipitation. The pellet was dissolved in small quantity of extraction buffer and directly loaded on the sepadex G-100 gel filtration column.

Mannosidase was assayed in one ml of the reaction mixture consisting of 940 µl of MQ, 20 µl of 20 mM substrate (pNP-α-D-mannopyrinoside) and 20 µl aliquot of the enzyme at 37° C. for 15 min along with a blank devoid of the enzyme. The reaction was stopped by adding of 40 µl of 0.5M $Na_2CO_3$. The colour developed as result of pNP release was recorded at 405 nm and quantified using a standard curve.

Example 2

2-Dimensional Gel Electrophoresis, SDS-PAGE and Immunoblot Analysis

Isoelectric focusing was carried out with 20 µg of purified protein sample in 250 L 2-D rehydration buffer for 13 cm gel strips. Proteins were first separated according to their charge after passive rehydration on 13 cm long immobiline dry strips, pH 4-7. Electrofocusing was performed using IPGphor system (Amersham Biosciences) at 20° C. for 20,000 Vhrs. The focused strips were subjected to reduction followed by alkylation with 1% (w/v) DTT and 2.5% (w/v) iodoacetamide, respectively in 10 ml of equilibration buffer. The strips were then loaded on top of 12.5% polyacrylamide gels for second dimensional separation on SDS-PAGE. The electrophoresed proteins were stained with silver stain plus kit (Bio-Rad, CA, USA). The spots were cut from the gel and analyzed by electrospray ion trap time-of-flight mass spectrometry (LC-MS/MS) (Q-Star Pulsar i, Applied Biosystems). The spectra were analyzed by mascot sequence matching software (Matrix Science) against the Viridiplantae (green plants) database.

For immunoblot analysis 50 μg of total protein from different stages of ripening was quantified and loaded on to 12.5% SDS-PAGE gel. After electrophoresis the gel was transferred to Hybond-C (Amersham) membrane at constant current of 150 mA. Non specific sites on the membrane were blocked by Blotto in Tris Buffer Saline (TBS) for 1 hr and incubated with the primary antibody overnight at 4° C. Immunodetection was carried out with horse radish peroxidase conjugated anti-rabbit antiserum as secondary antibody for 1 hr and exposing the bolt to chemiluminescence substrate (Pierce Biotechnology).

On SDS PSGE tomato mannosidase resolved into two subunits of 70 and 40 kD. However, the size of native protein was found to be 360 kD on native PAGE.

Immunoblot analysis during different ripening stages of tomato confirmed maximum mannosidase protein accumulation at breaker stage of tomato

Example 3

Glycoprotein Staining and EndoH Digestion

Glycoprotein staining was performed according to manufacturer's instruction (of GelCode® Glycoprotein staining kit, PIERCE biotechnology). Endo H digestion was performed according to manufacturer's instruction (New England Biolabs). After the reaction it was resolved on 12.5% SDS PAGE, blotted on to nitrocellulose membrane and detected with mannosidase antibody.

The staining experiment confirmed that mannosidase is a glycoprotein with 2-3 kD glycan moetiy.

Example 3

Cloning, Characterization and Northern Hybridization

Degenerate primers were designed using the peptide tags and motifs identified by multiple sequence alignment. The amplified fragment was cloned in pGEM T-Easy vector and sequenced. Then the remaining 5' and 3' regions were amplified using RACE (Invitrogen).

Messenger RNA was isolated from seventy five microgram of the total RNA from all ripening stages using Dynabeads® mRNA purification kit (DYNAL biotech). The mRNA was resolved in 1.2% formaldehyde gel/1×MOPS at constant 50 volts, blotted onto a Hybond-N membrane (Amersham) and hybridized in phosphate buffer (0.5M NaPi pH 7.2, 7% SDS and). Hybridization was carried out for 12 hrs and the membrane was exposed to hyperfilm (Amersham) at −80° C. for 72 hrs.

Polypeptides encoding tomato mannosidase and capsicum mannosidase were cloned in pGEM-T Easy vector and named as pGMT and pGMC respectively.

Example 4

Immunolocalisation

The fruits at mature green and breaker stage were harvested and 5 mm×5 mm pieces of pericarp were fixed in 4% paraformaldehyde overnight. Next day the sections were washed with 1×PBS and mounted on to the cryostat (Lieca CM1510S). The frozen tissue was sectioned (10-15 μm) and dried on the slide at room temperature for 1 hr. The slides were washed with 1×PBS followed by incubation in 3% BSA to block the non-specific sites for 1 hr at room temperature and washed with 1×PBS for three times. The slides with the fruit pericarp sections were incubated overnight at 4° C. with polyclonal antibody of mannosidase. Next day the sections were washed three times with 1×PBS and incubated with secondary antibody labeled with FITC for three hours. The sections were then washed with 1×PBS for 8 times at 10 min interval. Then the samples were viewed in fluorescence microscope with appropriate filter. This confirmed that mannisidase is a cell wall protein.

Example 5

High Performance Anion Exchange Chromatography

One μg of protein was incubated with 100 ng each of N-linked oligosaccharides (Dextra, U.K) at 37° C. overnight and the sample was filtered through PVDF membrane to remove the enzyme. 10 μl of the filtered sample was used for the analysis. An HPAE-PAD system (Dionex DX 500 BioLC) equipped with a gradient pump (GP 40), an anion exchange column (Carbopac PA-1, 4×250 mm) an eluant degas module (EDM-2) for pressurizing the eluants with argon was used for the analysis of monosaccharides. The separated monosaccharides were detected by an ED 40 detector equipped with a gold electrode and an Ag/AgCl reference electrode. The resulting chromatographic data was integrated and plotted using a PC based oracle 2 data acquisition system (Indtech Analytical, Bombay), The standard (mannose) was injected at a concentration of 100 nmoles before and after the analysis of each sample to confirm the results. This confirmed the N-glycan processing ability of mannosidase

Example 6

RNAi/Antisense/Overexpression/MYMIV Plasmid Construction and *Agrobacterium* Based Transient Transformation Mannosidase was silenced using pHANNIBAL (with ampicillin resistance in bacteria) vector. Antisense construct was prepared in pBI 121 by replacing GUS gene and cloning mannosidase full length in reverse orientation. For VIGS vector 600 bp was cloned in MYMIV vector by replacing the GFP sequence. Over expression construct consisted of full length mannosidase gene cloned in PK7FWG2 vector by gateway cloning method. For agroinjection *agrobacterium* pre-cultures (3 ml) were grown for 24 hrs from individual colonies at 28° C. in YEP (Yeast extract 1%, peptone 1% and NaCl 0.5%) media with antibiotics. $\frac{1}{10}^{th}$ of this culture was transferred to 50 ml induction medium (0.5% beef extract, 0.1% yeast extract, 0.5% Peptone, 0.5% Sucrose, 2 mM $MgSO_4$, 20 mM acetosyringone, 10 mM MES, pH 5.6) with antibiotics and grown overnight. Next day the culture recovered by centrifugation and resuspended in infiltration medium (10 mM $MgCl_2$, 10 mM MES, 200 mM acetosyringone, pH 5.6) and incubated at room temperature with gentle agitation for 4 hrs. Then the culture was agroinjected into the fruits, using 1 ml syringe with 0.5-mm needle, by introducing the needle 1 to 2 mm deep near the stylar apex and gently injecting.

Example 7

RNA Isolation and Quantitative Real Time RT-PCR

RNA was isolated according to the Lithium chloride method and quantified using nanodrop (ND-100). 5 μg of total RNA was reverse transcribed to cDNA using superscript II (Invitrogen). Quantitative RT-PCR was performed using light Cycler Version 4.05 (Roche diagnostics) with cyber green. The cycle consisted of initial 10 min Taq activation at 95° C. followed by 45 cycles, consisting of 10 s at 94° C., 10 s at 55° C. and 10 s at 72° C. Then the melt curve analysis was performed to verify the fidelity of the amplification. Using the $2^{-\Delta\Delta}$ CT method, the data is presented as the fold change in gene expression normalized to an endogenous reference gene and relative to the control. The gene encoding actin was used as the endogenous control.

Example 8

Small RNA Isolation and Northern Hybridization

Total RNA was isolated as described previously. After precipitating the RNA with LiCl, it was washed with 70% ethanol and the pellet was air dried. Then the pellet was dissolved in 1ml of DEPC water and heated upto 65° C. for 5 min, and chilled on ice for 2 min. To precipitate the high molecular weight RNA, polyethylene glycol (molecular weight 8000) and NaCl was added to a final concentration of 5% and 0.5 M, respectively. After 30 min incubation on ice, the RNA was centrifuged at 13,000 rpm for 30 min. The supernatant was separated and precipitated with 3 volumes of ethanol and $\frac{1}{10}$ volume of 3M Sodium acetate (pH 5.2). The tube was placed in −20° C. overnight. Next day the low molecular weight RNA was precipitated by centrifugation at 13,000 rpm for 10 min. The pellet was dried and dissolved in 50 μl of DEPC water and resolved on 15% urea PAGE for 4-5 hrs at 70 V. Then the gel was transferred to nylon membrane using 0.5×TBE for 1 hr at 100V constant. The membrane was UV cross-linked and pre-hybridized in 50% formamide, 7% SDS and 50 mM $Na_2HPO4/NaH_2PO4$ pH 7.2 at 40° C. After 4 hours the denatured probe was added and hybridized for 14-16 hrs at 30° C. The blot was washed using 2×SSC and 1% SDS for 2 min at RT, then washed with 0.5×SSC and 0.1% SDS and exposed to the film. Gene specific siRNA of 21-23 nucleotides were detected in the RNAi fruits confirming RNAi mediated silencing of mannosidase.

Example 9

Tomato Transformation

To generate transgenic tomato plants, cotyledons from two-week-old seedlings were used as described. The tomato seeds were sterilized using 4% commercial bleach and germinated on Murashige and Skoog (MS) medium. After 2 weeks of germination the cotyledons were cut and cocultivated for 30 min with *A. tumefaciens* strain EHA105 containing different constructs. Then the cotyledons were collected for selection on MS plates containing 50 mg/l kanamycin. When the plantlets regenerated they were transferred to rooting medium. After rooting the plants were shifted to green house and were grown to maturity.

Example 10

Textural Analysis

Fruit firmness was determined using TA-XT Plus (Stable Microsystems UK). Each fruit was analyzed with 75 mm wide P75 compression plate and compressed to a vertical displacement of 5 mm and 10 mm with the test speed of 1 mm Firmness was defined as the response force to a 5 g applied force. The values were subjected to t-test to determine statistical significance. These results showed that the RNAi fruit has 2.5 times more firmness than the non transgenic fruits.

Example 11

Geraniol/ACC Treatment to the Seedlings

Pusa Ruby seeds were sterilized and germinated on MS medium. After 15 days the seedlings were transferred to a liquid media containing 10 mM geraniol in 20% DMSO or 1 mM ACC (1-aminocyclopropane-1-carboxylic acid) in water. The RNA was isolated from the harvested sample and reverse transcribed to cDNA for real-time RT-PCR analysis. Expression was calculated relative to the control seedlings (0 hr). The results showed that mannosidase is upregulated by geraniol and ethylene.

Example 12

Staining and Miroscopy

Sections were cut in cyrostated microtome (Leica 1050) and were allowed to dry on the slides. The slides were dipped in aqueous solution of 0.05% toluidine blue (sigma) in 0.1 M phosphate buffer at pH6.8 for 2 min and washed in water for 2 minutes. The stained sections were mounted in water under a cover slip and photographed at 100× magnification using Nikon 80i epiflouresent/phage contrast/bright field microscope.

To examine wall structure, sections were immersed 0.05% calcofluor, an optical brightener which binds to polysaccharides and washed in distilled water. The sections were examined with appropriate filter. The intense light-blue flouresecence was produced by calcofluor bound to components of the cell walls.

```
                                              SEQ ID NO: 1
cDNA of tomato α-mannosidase including 5' and
3' UTR region
GAGAGATTTGGGGTTTATGGTTTAGTACATTCTCTTTCAGTGAACACTCT

CAGCAATTGTGGAAATGAAAAATATGGGGAAGTTTGAAATTTGGTTCTTG

ATTTTGATGGTTTGTGGGTTGTGGGTAGTGGAAGCTAAGTATATGGTTTA

CAATACATCACAGGGAATTGTTTCAGGGAAGCTTAACGTTCATTTGGTTC

CTCACACTCACGATGATGTTGGCTGGTTGAAAACGGTCGATCAGTACTAT

GTTGGTTCCAACAATTCCATTCAGGTGGCTTGTGTTCAAAATGTCTTGGA

TTCATTGATTCCAGCATTATTGGCTGATAAAAACAGAAAGTTCATTTATG

TTGAACAGGCTTTTTTCCAGCGTTGGTGGAGGAATCAGAGCCCGGGAATG

CAGAGCACAGTCAAACAGCTCGTCAACTCGGGTCAACTTGAGTCCATAAA

TGGAGGTTGGTGCATGCATGATGAGGCAGCAACACATTATATTGACATGA

TAGATCAGACAACTCTAGGGCATAAATACATCAAACAACAGTTCAATGTT

ACTCCTAGAATTGGCTGGCAAATCGACCCTTTTGGGACATTCTGCTGTTC

AGGCATACCTTCTGGGAGCAAGGGTTGGATTCGACTCTCTTTTCTTTGGG

ACGCATTGACTACCAAGGACAGAGAAAAGAGGAAAATTGAGAAGAGCCTT

GAGGTCATTTGGAGGGGTTCTAAGAGTCTCAGTTCATCCACGCAAATATT

TTCAGGTGCATTCCCTCAGAATTATGAACCTCCCAGCAAATTTTACTTTG
```

-continued

```
AAGTGAATGATGATAATTCTCTTCCTGTTCAGGATGATGTCAACCTGTTT
GACTACAATGTCCAAGAGCGGGTCAATGACTTTGTTGCTGCTGCTTTGTC
CCAAGCCAATATCACTCGCACAAATCATATAATGTGGACCATGGGAACCG
ACTTCAAGTACCAATATGCTCATACATGGTTTCGGAATATGGACAAGCTC
ATTCACTACGTAAACCAAGATGGTCGTGTCAATGCTTTATATTCAAGCCC
TTCAATTTATACTGATGCAAAGTATGCTTTGGACGAGTCATGGCCTCTCA
AGACGGATGACTATTTCCCGTACGCAGACCGTATTAATGCTTATTGGACT
GGATACTTTACAAGTAGGCCTGCTCTCAAACTCTATGTTAGAATGATGAG
TGGCTATTATTTGGCAGCAAGGCAATTAGAATTCTTTAAAGGAAGAATTG
AGACAGGACCAACAACCGAAATATTGGCTGATGCCCTAGCCATCGCTCAA
CATCATGATGCTGTCAGTGGCACTCCAAAGCAACATGTTGCTGATGATTA
TGCCAAACGACTGTTCATAGGTTACAAGCAGGCTGAGGATTTAGTGTCTA
ATTCACTTGCTTGTATGGTGGAATCAGCTTCAGCATCTGGATGCAAGAAT
CCTCAGATAAATTTCAAGCAGTGCCCGTTGTTGAATATAAGTTATTGTCC
CCCAACAGAAGCTGATCTTGCTCCAGGCAAAAAATTAGTGGTTGTCGTGT
ACAATGCTCTTGGGTGGAAAAGAACAGATGTTGTCAGAATCCCTGTCGTC
AATAAGAATGTCATCGTTGAGGATTCCACTGGAAAAGAAATTGAATCACA
GCTTCTTCCAATAGTTAAAGAATCAATAGTAATAAGGAACTACTATGCTG
CAGCATACTTTGGTGAATCCCTACATCAAGCCCCAAATATTGGCTTGTG
TTTACAGCCACTGTTCCACCTTTGGGCTTTAGCTCCTATGTTATAACAAG
TGGTAAACAAGCAGTTGCTGCTTCAATACCACAGACGTTCTACAAAACTG
ATGGAAGTCAAAGTGATGCAGTAGAAGTGGGGCCGGGGAACTTGAAACTG
TTATATTCTGCAAATGGGGCAAAGTTTACTCAATATTTTAATAAGAGAAA
CCAGGTTAGAAGCTCTTTGGAGCAATCATTCAGTTATTATTCTGCAGACG
ATGGAAGCAAGGATGATTATAAAGACATTCAGGCATCTGGAGCATATGTG
TTTCGCCCAAACGGCTCATTCCCATCCACCCTGAGGGAAAGGTCCCAGC
TACCATTCTACGAGGTCCGCTGCTAGATGAAGTTCATCAAAATATCAATT
CATGGATATATCAGATCACTAGAGTGTACAAGGAAAAGGAGCACGTTGAA
GTTGAGTTCACTGTTGGCCCCATACCTATTGACAATGGAATTGGGAAAGA
GCTGGTGACTCAGATTCAAACTGACATCAAAAGCAACAAAACATTCTACA
CAGACTCTAATGGACGTGATTTCCTTAAAAGAGTTCGGGATTATAGAGCT
GACTGGGATCTTCAAGTGAACCAACCTGCTGCTGGAAATTATTATCCTAT
CAATCTTGGACTTTTCCTAAAGGACAACAACAACGAGTTCTCAGTTTTGG
TTGATAGATCTGTAGGTGGATCCAGCCTTGTTGATGGCCAATTGGAGCTA
ATGCTTCACCGGAGGTTACTCAATGATGATGGAAGAGGTGTTGCTGAAGC
ACTGAATGAAACCGTCTGTGCTCTTGGAAAATGCATGGGCTTGACTGTCC
AAGGCAAGTACTATATCCGGATTGATTCTCTTGGAGAGGGAGCGAAATGG
CGGCGGTCATTTGGACAGGAGATATATTCTCCATTGCTTCTAGCTTTTAC
TGAGCAGGATGGAGATAAATTTACAAAATTTCCAGTTCCAACCTTTTCAG
GGATGGACCCATCTTACAGTCTGCCTGATAATGTTGCAATAATTACGCTT
```

```
CAGGAGCTTGAAGATCACACCGTCCTCCTGAGATTGGCTCATTTATACGA
GGTTGATGAGGATAAGGATCTATCCACCAAGGCAAGTGTAGAATTGAAAA
GATTGTTCCCAAAGAGGAAGATAAACAAGATTAGAGAGATGAGTTTATCT
GCCAACCAAGAAAGAGTAGAAATGGAGAAGAAGAGATTAAAGTGGAAAGC
AGAGGCTCCTAGTGATTTGCGAGACGTGGCAAGAGGGGGACCTGTTGATC
CTACAAAGCTGATGGTAGAGCTCGCCCCAATGGAAATTCGCACCTTTGTT
ATTGATCTCAGCCAGAGCGTGCCAGAAGGTTGGAAGTCACATATGTCTCT
ATGATAGCAGTCTCCTGCAGCAGTCCAATCCAATCCGAATCGTCAAGACG
TCAAAGGGTATATGAGCAGCTTGAAACCTTCTTGGGACCTATTTGCCTG
TGTTGATATCACCTTGAGGAGGCAGCATTGAGTCTCTTGTTAGAAGATGT
GTTATCCTTTTTGTAATGGAATGAAAACCTCTTTGACAGAACAATAAACT
TATAATAATAATAATGATGTTGAAGAGAGAACTTCCATGTCTTAGCAAAA
AAAAAAAAAA
```

SEQ ID NO: 2
Protein sequence of tomato α-mannosidase
```
MKNMGKFEIWFLILMVCGLWVVEAKYMVYNTSQGIVSGKLNVHLVPHTHD
DVGWLKTVDQYYVGSNNSIQVACVQNVLDSLIPALLADKNRKFIYVEQAF
FQRWWRNQSPGMQSTVKQLVNSGQLESINGGWCMHDEAATHYIDMIDQTT
LGHKYIKQQFNVTPRIGWQIDPFGTFCCSGIPSGSKGWIRLSFLWDALTT
KDREKRKIEKSLEVIWRGSKSLSSSTQIFSGAFPQNYEPPSKFYFEVNDD
NSLPVQDDVNLFDYNVQERVNDFVAAALSQANITRTNHIMWTMGTDFKYQ
YAHTWFRNMDKLIHYVNQDGRVNALYSSPSIYTDAKYALDESWPLKTDDY
FPYADRINAYWTGYFTSRPALKLYVRMMSGYYLAARQLEFFKGRIETGPT
TEILADALAIAQHHDAVSGTPKQHVADDYAKRLFIGYKQAEDLVSNSLAC
MVESASASGCKNPQINFKQCPLLNISYCPPTEADLAPGKKLVVVVYNALG
WKRTDVVRIPVVNKNVIVEDSTGKEIESQLLPIVKESIVIRNYYAAAYFG
ESPTSSPKYWLVFTATVPPLGFSSYVITSGKQAVAASIPQTFYKTDGSQS
DAVEVGPGNLKLLYSANGAKFTQYFNKRNQVRSSLEQSFSYYSADDGSKD
DYKDIQASGAYVFRPNGSFPIHPEGKVPATILRGPLLDEVHQNINSWIYQ
ITRVYKEKEHVEVEFTVGPIPIDNGIGKELVTQIQTDIKSNKTFYTDSNG
RDFLKRVRDYRADWDLQVNQPAAGNYYPINLGLFLKDNNNEFSVLVDRSV
GGSSLVDGQLELMLHRRLLNDDGRGVAEALNETVCALGKCMGLTVQGKYY
IRIDSLGEGAKWRRSFGQEIYSPLLLAFTEQDGDKFTKFPVPTFTGMDPS
YSLPDNVAIITLQELEDHTVLLRLAHLYEVDEDKDLSTKASVELKRLFPK
RKINKIREMSLSANQERVEMEKKRLKWKAEAPSDLRDVARGGPVDPTKLM
VELAPMEIRTFVIDLSQSVPEGWKSHMSL
```

SEQ ID NO: 3
cDNA sequence of capsicum α-mannosidase
including 5' and 3' UTR region
```
GAATTTATTTGGTATTTATTTCCAATTAATTAATTAATTAATGTAGTAG
TAGGTCCTTTGTCTTTGATTCCCCTTCATGTTTTGTCTACAAATTTCAGC
AGCCTATTTATAAAGACATTGAGTGCACACTCATAGCAAATTTGTGAAAT
GAAAGATATGGCTAAGTGTGAAATTTGGTTCTTGATTTTGATGCTTTGTG
```

-continued

```
GGTTGGTGGTGGAAGCAAAGTATATGGTTTACAATACATCACAAAGCATT
GTTAAAGGGAAGCTTAATGTTCATTTGGTTCCTCACAGTCATGATGATGT
TGGCTGGTTGAAAACTATCGATCAGTACTATGTTGGATCCAATAATTCCA
TTCAGGGAGCTTGTGTTGAAAATGTCTTGGATTCAATGGTTCCAGCATTA
TTGGCTGATAAAAACCGGAAGTTCATTTATGTTGAACAGGCTTTTTTCCA
GCGTTGGTGGAGGAATCAGAGCCCCGAAATTCAGAGCACAGTTAGGCAGC
TTATCAACTCGGGTCAACTTGAGTTCATAAACGGAGGTTGGTGCATGCAT
GACGAGGCAGCGACACATTATATTGACATGATAGATCAGACAACTCTAGG
GCACAGATACATCAAACAACAGTTCAATATTGCTCCAAGAATTGGCTGGC
AAATTGACCCTTTTGGACATTCTGCTGTTCAGGCATACCTTCTGGGAGCA
GAGGTTGGATTCGACTCTCTTTTCTTTGGACGCATTGACTACCAAGACAG
AGAAAAGAGGAAATTGAGAAGAGCCTTGAGGTCATTTGGAGGGGTTCTA
AGAGTCTCAGTTCATCCACGCAAATATTTTCAGGTGCATTCCCTCAGAAT
TATGAACCTCCCAGCAAATTTTACTTTGAAGTGAATGATGATAATTCTCT
TCCTGTTCAGGATGATGTCAACCTGTTTGACTATAATGTCCAAGAGCGGG
TCAATGACTTTGTTGCTGCTGCTTTGTCCCAAGCCAATATCACTCGCACA
AATCATATAATGTGGACCATGGGAACCGACTTCAAGTACCAATATGCTCA
TACATGGTTTCGGAATATGGACAAGTTCATTCACTACGTAAACCAAGATG
GTCGTGTCAATGCTTTATATTCAAGCCCTTCAATTTATACTGATGCAAAG
TATGCTTTGGACGAGTCATGGCCTCTCAAGACGGGTGACTATTTCCCGTA
CGCAGACCGTATTAATGCTTATTGGACTGGATACTTTACAAGTAGGCCTG
CTCTCAAACTCTATGTTAGAATGATGAGTGGCTATTATTGGCAGCAAGG
CAATTAGAATTCTTTAAAGGAAGAAGTGAGACAGGAGGACCAACAACCGA
AGTGTTGGCTGATGCGCTTGCCATTGCCCAGCATCATGATGCTGTCAGTG
GCACTTCAAAGCAACATGTTGCTGATGATTATGCCAAACGACTGTTCATA
GGTTACAAGCAGGCTGAGGATATAGTGTCAAATTCACTCGCTTGTATGGT
GGAACCAGCTTCAGCATCTGGATGCAAGAATCCTCGGATTAATTTCAAGC
AGTGCCCATTGTTGAATATAAGTTATTGTCCCCCAACAGAAGCTGATCTT
GCTCCTGGCAAAAAATTAGTGGTTGTCGTGTACAATGCTCTTGGGTGGAA
AAGAACAGATGTTGTCAGAATCCCTGTTGTCAATAAGAATGTCATCATTC
AGGATTCCACTGGAAAAGAAATTGAATCACAGCTTCTTCCAATAGTTAAA
GCTTCAATAGCAATAAGGAACTACTATGCTACCGCATATGTTGGTGAATC
ACCTACATCAAGCCCCAGATATTGGCTCGTGTTTACAGCTACTGTTCCAC
CATTGGGCTTTAACTCCTACATTATATCAAGTGGTAAACAAGCAGTTGCT
GCTTCAATACCACAGTCTTTCTACAAAACTGATGGAAGTCAAAGTGATGT
TATAGAAGTGGGGCCCGGGAACTTGAAACTGTTATATTCTGCAAATGGGG
GAAAGTTCACTCAATATTTTAATAAGAGAAACCAGGTTAGAAGCTCTCTG
GAGCAATCATTCAGTTATTATTCTGCAGATGATGGAAGCAAGGATGCTTA
TAAAGACATTCAGGCCTCTGGGGCATATGTGTTTCGTCCAAATGGCTCAT
TCCCCATCCACCCCGAGGGAAAGGTTCCAGCTACCATTCTGCGAGGTCCG
```

```
CTGCTAGATGAAGTTCATGAAAATATTAATTCATGGATATATCAGATCAC
TAGAGTGTACAAGGAGAAGGAGCACGTTGAAGTTGAGTTCACTGTTGGCC
CCATACCTATTGACAATGGAATTGGGAAAGAGCTGGTGACTCAGATTCAA
ACTGACATCAAAAGCAACAAAACATTCTACACCGACTCTAATGGACGTGA
TTTCCTCAAAAGGATTCGGGATTACAGAGCTGATTGGGATCTTCAAGTGA
ACCAACCTGCTGCTGGAAATTATTATCCTATTAATCTTGGAATTTTCCTG
AAAGACGACAGCAACGAGTTCTCAGTTTTGGTTGATAGATCTGTAGGTGG
ATCCAGCCTTGTTGATGGCCAATTGGAGCTAATGCTTCACCGGAGGTTAC
TCCATGATGATGGAAGAGGGGTTGCTGAAGCACTGAATGAAACAGTCTGT
GCTCTTGGAAAATGCATGGGCTTGACTGTCCAAGGCAAGTACTATATCCG
GATTGATTCTCTGGGAGAGGGAGCAAAGTGGCGGAGGTCATTTGGACAGG
AGATATATTCTCCGTTGCTTCTAGCTTTTACTGAGCAGGATGGAGATAAA
TTTACAAAATTTCCAGTTCCAACATTTACATGGATAGATCCATCTTACAG
TCTGCCTGATAATGTTGCAATAATCACCCCTTCAGGAGCTTGAAGATCACA
CTGTCCTCCTCAGATTGGCTCATTTATACGAGGTTGATGAGGATAAGGAT
CTGTCCACCAAGGCAATTGTAGAATTGAAGAGATTGTTCCCAAAGAGAAA
GATAAACAAGATTAAAGAGATGAGTTTATCTGCCAACCAAGAAAGAGAAG
AAATGAAAAGAAGAGATTGAAGTGGAAAGCAGAGGCTCCTAGTGATTCG
CAAGACGTGCCAAGAGGGGGACCTGTTGATCCTACAAAGTTGGTGGTGGA
GCTTGCCCCAATGGAAATCCGCACTTTCGTTATCAACCTCGGCCAGAGCT
CGCCAGCTCCAGGAGGTTGGAAGTCACACATGTCTCTATGATAGCGGTGC
CCCTGAAACAGTCCAATCCGATTCGGCTAGACAGCAAAAGGGTATGGGCA
GCTTGAAACCTACTTGGGACCTATTTGCCTATGTTGATCCTTGAGGATGC
AACATTGAGTCTCTTGTTGGAAGATGTGTTATCCTTTTTGTATAAGGAAT
GAAAACCTCTTTGGCAGAACAATAACTTACTCTATAATAATAAATAATAA
TGTTGAAGAGAAAAAAAAAAAAAAAAAA
```

SEQ ID NO: 4
Protein sequence of caspicum α-mannosidase

```
MKDMAKCEIWFLILMLCGLVVEAKYMVYNTSQSIVKGKLNVHLVPHSHDD
VGWLKTIDQYYVGSNNSIQGACVENVLDSMVPALLADKNRKFIYVEQAFF
QRWWRNQSPEIQSTVRQLINSGQLEFINGGWCMHDEAATHYIDMIDQTTL
GHRYIKQQFNIAPRIGWQIDPFGHSAVQAYLLGAEVGFDSLFFGRIDYQD
REKRKIEKSLEVIWRGSKSLSSSTQIFSGAFPQNYEPPSKFYFEVNDDNS
LPVQDDVNLFDYNVQERVNDFVAAALSQANITRTNHIMWTMGTDFKYQYA
HTWFRNMDKFIHYVNQDGRVNALYSSPSIYTDAKYALDESWPLKTGDYFP
YADRINAYWTGYFTSRPALKLYVRMMSGYYLAARQLEFFKGRSETGGPTT
EVLADALAIAQHHDAVSGTSKQHVADDYAKRLFIGYKQAEDIVSNSLACM
VEPASASGCKNPRINFKQCPLLNISYCPPTEADLAPGKKLVVVVYNALGW
KRTDVVRIPVVNKNVIIQDSTGKEIESQLLPIVKASIAIRNYYATAYVGE
SPTSSPRYWLVFTATVPPLGFNSYIISSGKQAVAASIPQSFYKTDGSQSD
VIEVGPGNLKLLYSANGGKFTQYFNKRNQVRSSLEQSFSYYSADDGSKDA
```

YKDIQASGAYVFRPNGSFPIHPEGKVPATILRGPLLDEVHENINSWIYQI

TRVYKEKEHVEVEFTVGPIPIDNGIGKELVTQIQTDIKSNKTFYTDSNGR

DFLKRIRDYRADWDLQVNQPAAGNYYPINLGIFLKDDSNEFSVLVDRSVG

GSSLVDGQLELMLHRRLLHDDGRGVAEALNETVCALGKCMGLTVQGKYYI

RIDSLGEGAKWRRSFGQEIYSPLLLAFTEQDGDKFTKFPVPIFTWIDPSY

SLPDNVAIITLQELEDHTVLLRLAHLYEVDEDKDLSTKAIVELKRLFPKR

KINKIKEMSLSANQEREEMEKKRLKWKAEAPSDSQDVPRGGPVDPTKLVV

ELAPMEIRTFVINLGQSSPAPGGWKSHMSL

---

We claim:

1. A cDNA encoding a polypeptide having mannosidase activity wherein the amino acid sequence of the polypeptide is the amino acid sequence set forth in SEQ ID NO: 2.

2. A DNA construct comprising the cDNA as claimed in claim 1, wherein the cDNA is operably linked to a heterologous promoter sequence.

3. The DNA construct as claimed in claim 2, wherein the cDNA is in sense or anti-sense orientation.

4. An RNAi construct for suppressing mannosidase expression in a transgenic plant, said construct comprising as operably linked components,
   (i) a sense polynucleotide strand comprising at least 20 contiguous nucleotides of SEQ ID NO: 1 or SEQ ID NO: 3 operably linked to a heterologous promoter in the sense orientation,
   (ii) a spacer sequence,
   (iii) the polynucleotide strand of (i) in the anti-sense orientation, and
   (iv) a transcription terminator sequence.

5. A recombinant vector comprising the DNA construct as claimed in claim 2.

6. A recombinant vector comprising the RNAi construct as claimed in claim 4.

7. A recombinant host cell comprising the recombinant vector as claimed in claim 5 or 6.

8. The recombinant host cell as claimed in claim 7 wherein the host cell is selected from the group consisting of *Agrobacterium*, *E. coli*, and yeast.

9. A process for delaying fruit softening in a plant, said process comprising transforming a plant cell, tissue or any part thereof with a recombinant vector comprising a DNA construct comprising a cDNA encoding a polypeptide having the amino acid sequence as set forth in SEQ ID NO: 2 or SEQ ID NO: 4 operably linked to a heterologous promoter, wherein said cDNA is in the anti-sense orientation.

10. The process as claimed in claim 9, wherein the nucleotide sequence of the cDNA is as set forth in SEQ ID NO: 1 or SEQ ID NO: 3.

11. A process for delaying fruit softening in a plant, said process comprising transforming a plant cell or tissue with a recombinant vector comprising an RNAi construct comprising: (i) a polynucleotide strand of at least 20 contiguous nucleotides selected from SEQ ID NO: 1 or SEQ ID NO: 3 operably linked to a heterologous promoter in the sense orientation; and (ii) the polynucleotide from (i) in the anti-sense orientation, wherein the sense and anti-sense strands hybridize to form a hairpin structure.

12. The process as claimed in claim 11, wherein the nucleotide sequence of the polynucleotide strand operably linked to a heterologous promoter in the sense or anti-sense orientation is the sequence of nucleotides 1-600 of SEQ ID NO: 1 or the sequence of nucleotides 2811-3411 of SEQ ID NO: 1.

13. A transgenic plant or a transgenic seed produced by the process as claimed in claim 9 or 11, wherein expression of an endogenous mannosidase in said plant is controlled to delay fruit softening.

14. The transgenic plant as claimed in claim 13 wherein the plant is tomato or capsicum.

15. The DNA construct as claimed in claim 2, wherein the polynucleotide sequence of the cDNA is the sequence of nucleotides 65-3154 of SEQ ID NO: 1.

16. The RNAi construct as claimed in claim 4 wherein the nucleotide sequence of the polynucleotide strand operably linked to a heterologous promoter in the sense or anti-sense orientation is the sequence of nucleotides 1-600 of SEQ ID NO: 1 or the sequence of nucleotides 2811-3411 of SEQ ID NO: 1.

17. The process of claim 9 wherein the nucleotide sequence of the cDNA is the sequence of nucleotides of 65-3154 of SEQ ID NO: 1.

18. A DNA construct comprising a cDNA encoding a polypeptide having mannosidase activity wherein the amino acid sequence of the polypeptide is the amino acid sequence set forth in SEQ ID NO: 4, wherein the cDNA is operably linked to a heterologous promoter.

19. The DNA construct as claimed in claim 18, wherein the cDNA is in the sense or anti-sense orientation.

* * * * *

UNITED STATES PATENT AND TRADEMARK OFFICE
CERTIFICATE OF CORRECTION

Page 1 of 1

PATENT NO. : 8,962,918 B2
APPLICATION NO. : 13/003203
DATED : February 24, 2015
INVENTOR(S) : Asis Datta et al.

It is certified that error appears in the above-identified patent and that said Letters Patent is hereby corrected as shown below:

In the Claims:

At Column 43, line 63, "a sense polynucleotide" should be -- a polynucleotide --.

At Column 45, line 13, "strands" should be -- polynucleotide strands --.

Signed and Sealed this
Twenty-third Day of February, 2016

Michelle K. Lee
*Director of the United States Patent and Trademark Office*